(12) United States Patent
Fukuzawa et al.

(10) Patent No.: US 7,297,152 B2
(45) Date of Patent: Nov. 20, 2007

(54) LANCING APPARATUS

(75) Inventors: Masahiro Fukuzawa, Kyoto (JP);
Masufumi Koike, Kyoto (JP);
Takatoshi Uchigaki, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 10/493,984

(22) PCT Filed: Oct. 25, 2002

(86) PCT No.: PCT/JP02/11125

§ 371 (c)(1),
(2), (4) Date: Apr. 29, 2004

(87) PCT Pub. No.: WO03/037185

PCT Pub. Date: Aug. 5, 2003

(65) Prior Publication Data

US 2004/0260324 A1    Dec. 23, 2004

(30) Foreign Application Priority Data

Oct. 31, 2001 (JP) .............................. 2001-334145
Oct. 31, 2001 (JP) .............................. 2001-334146

(51) Int. Cl.
*A61B 17/32* (2006.01)
(52) U.S. Cl. .................................... 606/181
(58) Field of Classification Search ........ 606/181–183, 606/185, 167, 172; 600/583; 604/176, 9
See application file for complete search history.

(56) References Cited

U.S. PATENT DOCUMENTS 4,393,870 A * 7/1983 Wagner ...................... 604/115
5,613,978 A * 3/1997 Harding ...................... 606/181
5,666,966 A * 9/1997 Horie et al. ................. 600/573
5,730,753 A   3/1998 Morita
5,916,230 A * 6/1999 Brenneman et al. ........ 606/172

(Continued)

FOREIGN PATENT DOCUMENTS

EP    0 885 590    12/1998

(Continued)

OTHER PUBLICATIONS

Translation of document JP 2000-225110, Hisao et al.*

(Continued)

*Primary Examiner*—Anhtuan T. Nguyen
*Assistant Examiner*—Elizabeth Houston
(74) *Attorney, Agent, or Firm*—Hamre, Schumann, Mueller & Larson, P.C.

(57) ABSTRACT

The present invention relates to a lancing apparatus (A) comprising an apparatus body (1) including a housing (5) and a movable member for advancing a needle (40*b*), the movable member being arranged movably in the housing (5), and a plurality of front end covers (2, 3) each for coming into contact with a portion to be lanced in lancing. Preferably, the plurality of front end covers (2, 3) have different structures adapted for lancing different portions and are removably attachable to a same portion of the apparatus body (1) individually. A suitable cover (2 or 3) for the portion to be lanced is selectable from the front end covers (2, 3), and the selected front end cover (2 or 3) is attached to the apparatus body (1) in use.

20 Claims, 20 Drawing Sheets

U.S. PATENT DOCUMENTS

| | | | | |
|---|---|---|---|---|
| 6,071,249 A * | 6/2000 | Cunningham et al. | ...... | 600/578 |
| 6,071,251 A * | 6/2000 | Cunningham et al. | ...... | 600/584 |
| 6,086,545 A * | 7/2000 | Roe et al. | ...... | 600/570 |
| 6,093,156 A * | 7/2000 | Cunningham et al. | ...... | 600/573 |
| 6,152,942 A * | 11/2000 | Brenneman et al. | ...... | 606/181 |
| 6,261,245 B1 * | 7/2001 | Kawai et al. | ...... | 600/576 |
| 6,530,937 B1 * | 3/2003 | Schraga | ...... | 606/182 |
| 6,645,219 B2 * | 11/2003 | Roe | ...... | 606/182 |
| 6,929,650 B2 * | 8/2005 | Fukuzawa et al. | ...... | 606/182 |
| 7,131,984 B2 * | 11/2006 | Sato et al. | ...... | 606/182 |
| 2004/0059366 A1* | 3/2004 | Sato et al. | ...... | 606/182 |
| 2004/0068283 A1* | 4/2004 | Fukuzawa et al. | ...... | 606/181 |
| 2004/0158271 A1* | 8/2004 | Hamamoto | ...... | 606/181 |
| 2004/0186500 A1* | 9/2004 | Koike et al. | ...... | 606/181 |

FOREIGN PATENT DOCUMENTS

| | | | |
|---|---|---|---|
| JP | 11-9577 | | 1/1999 |
| JP | 2000-225110 | * | 8/2000 |
| JP | 2001-515377 | | 9/2001 |
| WO | WO 97/04707 | | 2/1997 |
| WO | WO 97/46157 | | 12/1997 |
| WO | WO 98/24366 | * | 6/1998 |

OTHER PUBLICATIONS

European Search Report for the corresponding EP 02777972.7, mailed Dec. 22, 2006.

* cited by examiner

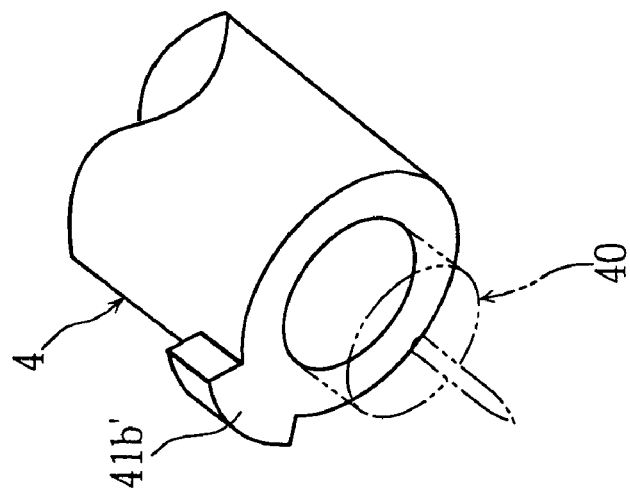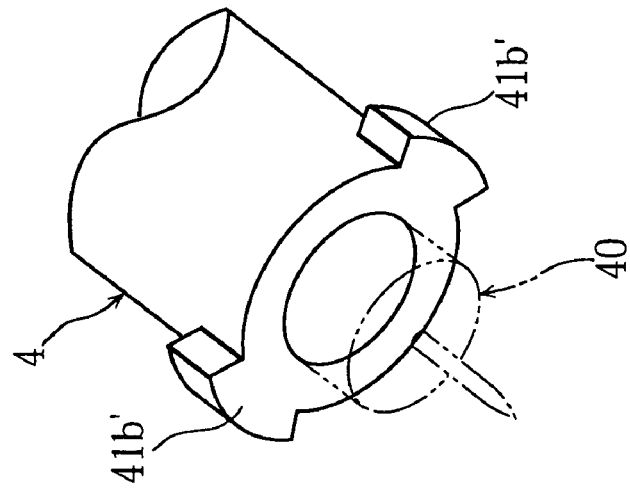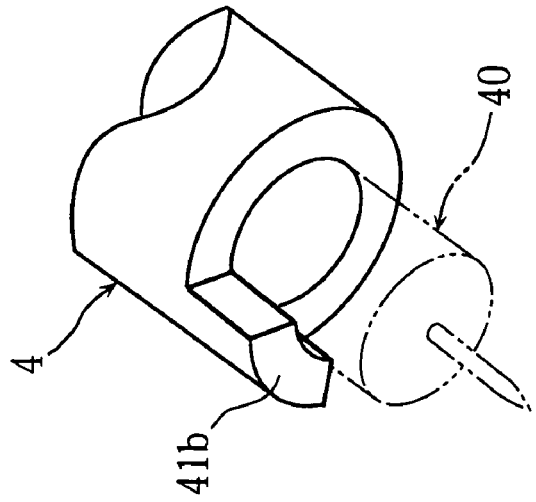

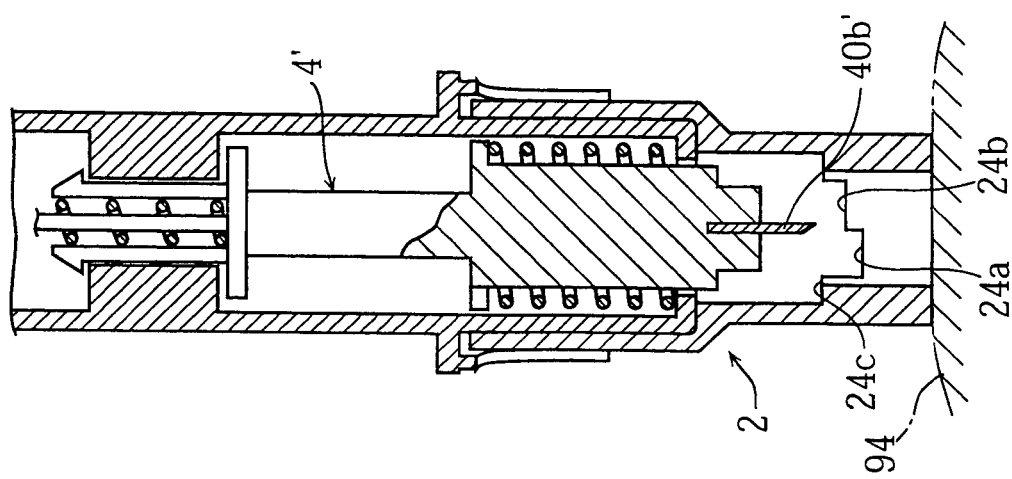
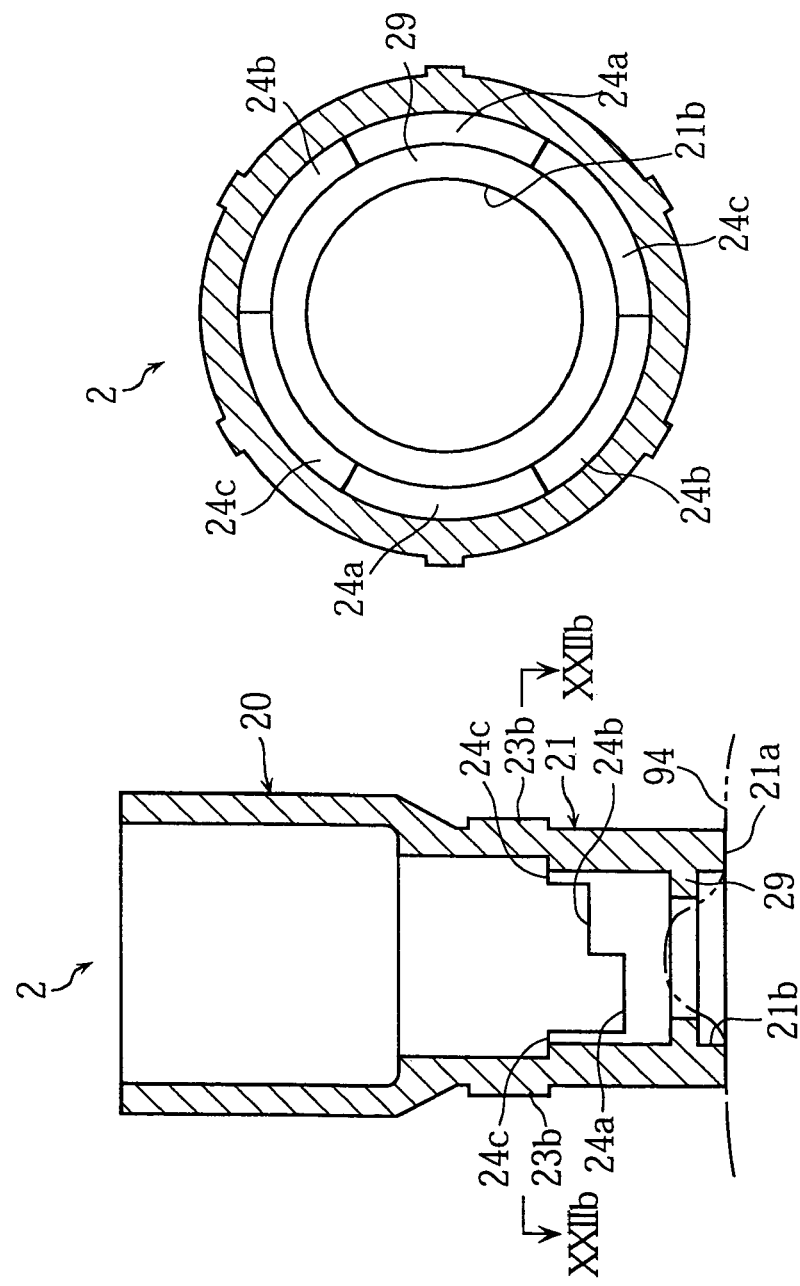

LANCING APPARATUS

TECHNICAL FIELD

The present invention relates to a lancing apparatus used to stick a tip end of a lancet into skin for extracting blood, other body fluid or tissue for testing.

BACKGROUND ART

In a typical lancing apparatus, a lancet holder holding a lancet is accommodated in a housing to which a front end cover is attached. When a predetermined operation is performed, the lancet holder advances toward the front end of the front end cover by a spring force. Since the lancet is generally disposable, the front end cover is made removable so that it can be removed in attaching or detaching the lancet. In using the lancing apparatus, the front end cover is pressed against skin of the human body. The front end cover is formed with an opening for allowing the needle to lance the skin. When the lancet holder is advanced, the lancet passes through the opening to lance the skin.

For example, blood is extracted from the fingertip or the forearm. Although, the fingertip bleeds easily, lancing of the fingertip involves relatively strong pain. On the other hand, although the forearm is unlikely to bleed, the pain in lancing is relatively small. Further, the tendency to bleed from the skin varies among individuals at any portion of the skin. Preferably, therefore, the portion of the skin for extracting blood is selected based on the user's preference or in consideration of the tendency to bleed. In extracting blood from the forearm, it is preferable to bulge the skin by suction and to lance the bulged skin for promoting bleeding.

However, when the same front cover is used for the blood extraction from the fingertip and that from the forearm, proper blood extraction may not be performed in the following reasons.

When a front end cover with a relatively large opening is pressed against the fingertip, the finger tip bulges. The amount of bulging differs among individuals because of the variations of the hardness of the skin. Therefore, the positional relationship between the needle of the lancet and the skin, and hence, the lancing depth differ among individuals, which hinders stable lancing operation. To eliminate such a problem, it is desirable to use a front end cover with a relatively small opening. On the other hand, in extracting blood from the forearm, it is preferable to bulge the skin by suction, as noted above. For this purpose, it is preferable to use a front end cover with a relatively large opening. Further, when a lancing apparatus having a manual suction mechanism is used, the positional relationship between the lancing apparatus and the skin is likely to deviate due to the vibration of the lancing apparatus during the suction. To perform stable lancing operation by preventing such deviation, the adhesion between the front end cover and the skin need be enhanced. Also for this purpose, it is preferable to use a front end cover with a relatively large opening.

As noted above, it is preferable to use a front end cover with a relatively small opening for the blood extraction from the fingertip, whereas it is preferable to use a front end cover with a relatively large opening for the blood extraction from the forearm. In the conventional lancing apparatus, however, the size of the opening of the front end cover is fixed. Therefore, to properly perform both of the blood extraction from the fingertip and that from the forearm, the user need to prepare a plurality of lancing apparatuses, i.e. one for the fingertip and one for the forearm, for example. Such preparation and use of a plurality of lancing apparatuses is inconvenient for the user and puts the financial burden on the user. However, with a single kind of lancing apparatus, proper blood extraction is possible only from a single particular portion, which is inconvenient.

In lancing the skin with a lancet by utilizing a lancing apparatus, it is desirable that the amount of lancing in the skin is adjustable for minimizing the pain the user feels and for preventing excessive or insufficient bleeding from the skin. For instance, WO97/04707 A1 discloses lancing assembly in which the lancing depth is adjustable. Specifically, the disclosed assembly includes an injector for launching a lancet, a cap attached to the injector and engageable with the lancet, a cover for coming into contact with the skin in lancing, and an adjuster for adjusting the distance between the cap and the cover. In this assembly, the distance between the cap and the cover is adjustable by turning the adjuster, whereby the lancing depth can be adjusted.

However, the lancing depth adjustment mechanism of the assembly requires three parts, i.e. the cap, the cover and the adjuster in addition to the injector. Such a large number of parts leads to an increase in the manufacturing cost. Moreover, in this assembly, the lancet is attached to the injector in a state separated from the assembly, and then the assembly is attached to the injector. Therefore, even when the lancing depth need be adjusted due to e.g. the change of the position to be lanced, the user may attach the assembly to the injector and launch the lancet without adjusting the lancing depth. In such a case, an excessive or insufficient amount of blood may be extracted or the user may suffer discomfort.

DISCLOSURE OF THE INVENTION

An object of the present invention is to provide a lancing apparatus which enables any user to properly extract blood from a selected portion without putting excessive financial burden on the user. Another object of the present invention is to provide a lancing apparatus which prevents the user from forgetting to perform the lancing depth adjustment and which is advantageous in terms of cost.

According to a first aspect of the present invention, there is provided a lancing apparatus comprising an apparatus body including a housing and a movable member for advancing a needle, the movable member being arranged movably in the housing, and a plurality of front end covers each for coming into contact with a portion to be lanced in lancing. The plurality of front end covers have different structures adapted for lancing different portions and are removably attachable to a same portion of the apparatus body individually, and one of the front end covers suitable for the portion to be lanced is selected in use for attachment to the apparatus body.

With this structure, the user can select and use a front end cover which is suitable for the portion which the user is to lance. Therefore, proper blood extraction from different portions is possible without the need for preparing a plurality of lancing apparatuses such as one for blood extraction from the forearm and one for blood extraction from the fingertip. This structure is not only convenient for the user but also reduces financial burden on the user, because preparation of a single lancing apparatus is sufficient. Further, the front end cover suitable for the portion to be lanced can be used just by selecting the cover, so that any user can perform stable blood extraction.

In a preferred embodiment, the lancing apparatus further comprises suction means for generating negative pressure in the front cover attached to the apparatus body. For instance, the front end covers include one having a through-hole for providing communication between the inside and the outside of the front end cover. Preferably, the plurality of front end covers include a first front end cover formed with a relatively large opening at an end for contacting a portion to be lanced, and a second front end cover formed with a relatively small opening at an end for contacting a portion to be lanced. In this case, it is preferable that the second front end cover is formed with a through-hole.

Since the above structure includes suction means, when blood is to be extracted from a portion which is unlikely to bleed (e.g. forearm), negative pressure can be applied to the portion by the suction means for promoting bleeding. In extracting blood from a portion which easily bleeds (e.g. fingertip), negative pressure may not be applied. When negative pressure is to be applied to the portion to be lanced, it is preferable to select and use the first front end cover having a relatively large opening. When the front end cover having a large opening is pressed against the portion to be lanced, the skin at that portion bulges, whereby the front end cover and the portion to be lanced contact closely with each other. Thus, the formation of a gap between the front end cover and the portion to be lanced can be prevented, so that the suction operation and the lancing operation can be performed reliably. When negative pressure is not applied to the portion to be lanced, it is preferable to use the second front end cover. Since the second front end cover has a relatively small opening, when the front end cover is pressed against the portion to be lanced, variations in the bulging degree among users due to variations of hardness of the skin at that portion are small. As a result, the positional relationship between the needle and the portion to be lanced can be made generally constant among the users, so that any user can perform the lancing operation properly.

The through-hole of the front end cover may have any configuration and may be formed at any position as long as it can provide communication between the inside and the outside of the second front end cover. Therefore, the through-hole referred to herein includes a cutout which is formed at the front end (the end for contacting the portion to be lanced) or the base end (the end to be attached to the apparatus body) of the second front cover and which opens in a direction crossing the hole-penetrating direction.

As noted above, the second front end cover is preferably used when negative pressure is not to be applied to the portion to be lanced. However, the user may erroneously apply negative pressure to the portion to be lanced while using the second front end cover. Even in such a case, the through-hole for providing communication between the inside and the outside allows air to flow into the second front end cover, whereby the application of large negative pressure to the portion to be lanced can be prevented.

In a preferred embodiment, the first front end cover includes a controlling portion for controlling the degree of bulging of the portion to be lanced when the portion to be lanced is bulged by generating negative pressure in the front end cover by the suction means.

With this structure, the bulging degree of the portion to be lanced during the suction can be made constant regardless of the softness of the portion to be lanced, so that the lancing operation can be performed reliably.

In a preferred embodiment, the lancing apparatus further comprises an operation casing accommodating the housing, and the operation casing is reciprocally movable axially of the housing relative to the housing. The suction means is capable of adjusting the negative pressure in accordance with the number of times of the reciprocal movement of the operation casing axially of the housing.

With this structure, excess bleeding or insufficient bleeding from the lanced portion can be prevented by adjusting the negative pressure to be applied to that portion. Further, even when negative pressure is not duly generated due to insufficient contact between the front end cover and the portion to be lanced or airtightness is lost after the generation of negative pressure, intended negative pressure can be generated by moving the operation casing again.

In a preferred embodiment, the lancing apparatus further comprises operation means for advancing the movable member, and after the movable member is advanced by operating the operation means, negative pressure generated by the suction means is relieved by further operating the operation means.

With this structure, when negative pressure is generated before the portion to be lanced is stuck by the needle, the negative pressure can be reliably applied to the portion until the sticking of the needle is completed. The relieving of negative pressure can be conveniently performed by utilizing the operation means for advancing the movable member.

In a preferred embodiment, the movable member is provided with a first contact portion, whereas each of the front end covers is provided with a second contact portion for contacting the first contact portion for controlling movement of the movable member toward the front-end side.

In this case, the lancing depth of the needle relative to the portion to be lanced is adjustable by selecting a contact position in the first contact portion or the second contact portion. With this arrangement, since the lancing depth in the portion to be lanced is adjustable, the user does not feel unnecessarily strong pain caused by unnecessarily large lancing depth. Further, since the lancing depth is adjustable in view of the portion to be lanced or the tendency to bleed of the user, excessive or insufficient bleeding can be prevented.

The lancing depth adjustment function can be realized just by providing a first contact portion in the movable member of the apparatus body and providing a second contact portion in the front end cover. The lancing apparatus body and the front end covers are necessary for making the lancing apparatus even when the lancing depth adjustment function is not to be provided. The first and the second contact portions can be formed just by changing the configuration of the apparatus body and the front end cover. Therefore, the lancing depth adjustment function can be provided without increasing the number of parts of the apparatus. For example, when the movable member and the front end cover are formed by resin molding, the first and the second contact portions can be formed just by appropriately designing the configuration of the mold used for the resin molding. In this way, according to the present invention, the lancing depth adjustment function can be provided easily without increasing the number of parts of the apparatus, which is advantageous in terms of the manufacturing cost.

Preferably, to reliably adjust the lancing depth, at least one of the first contact portion and the second contact portion includes a plurality of flat contact surfaces which differ from each other in distance from the front end surface of the selected front end cover when the front end cover is attached to the apparatus body. Alternatively, at least one of the first contact portion and the second contact portion includes a contact surface having a configuration providing a continuously varying distance between the contact surface and the front end surface of the front end cover. However, the first and the second contact surfaces may have any configuration as long as they can contact each other and adjust the lancing depth depending on the contacting portions.

In a preferred embodiment, the apparatus body is provided with a reference mark, whereas each of the front end covers is provided with one or a plurality of lancing depth adjustment marks. The lancing depth of the needle in the portion to be lanced is adjustable by selecting an alignment state of the adjustment mark or the adjustment marks with the reference mark in attaching selected one of the front end covers to the apparatus body. For example, when a plurality of lancing depth adjustment marks are provided, the alignment state between the reference mark and the adjustment mark can be selected by selecting the adjustment mark to be aligned with the reference mark. When a single adjustment mark is provided, the alignment state can be selected by selecting the portion of the adjustment mark to be aligned with the reference mark.

This structure is convenient, because the lancing depth can be adjusted in attaching the front end cover. The adjustment of the lancing depth can be performed easily just by selecting the alignment state between the reference mark and the adjustment mark.

In a preferred embodiment, each of the front end covers includes a plurality of projections. The housing includes a guide portion for engaging at least one of the projections to control movement of the selected front end cover when the front end cover is attached to the apparatus body, and an engagement portion for engaging at least one of the projections when the front end cover is turned circumferentially relative to the housing.

With this structure, the movement path of the projections of the front end cover is defined by the guide portion and the engagement portion, so that the front end cover can be reliably attached to the lancing apparatus body easily.

In a preferred embodiment, at least one of the projections is positioned at the guide portion when the lancing depth adjustment mark or selected one of the lancing depth adjustment marks is aligned with the reference mark.

With this structure, the lancing depth of the lancing apparatus can be set to the depth selected by the user more reliably.

In the lancing apparatus according of the present invention, the lancing depth of the needle in the portion to be lanced may be kept constant by causing the first contact portion to contact the second contact portion when the movable member is advanced. In such a case, the lancing operation providing stable lancing depth can be performed. In this case again, the first and the second contact portions may have any configuration as long as they can contact each other.

In a preferred embodiment, the needle is incorporated in the apparatus body as an integral part of a lancet, and the lancet is mounted to the movable member in a state in which the front end cover is not attached to the apparatus body.

In this case, the front end cover need be detached from the apparatus body before mounting the lancet and need be attached to the apparatus body after the lancet is mounted. Therefore, when a structure in which the lancing depth is to be adjusted in attaching the front end cover is employed, the selection of the lancing depth is necessary every time the lancet is mounted. With this arrangement in which the lancing depth is selected using the occasion of mounting the lancet, the lancing depth is set properly in each time of lancing, whereby just a sufficient amount of blood can be extracted without giving unnecessary pain to the user.

According to a second aspect of the present invention, there is provided a lancing apparatus with a lancing depth control function. The apparatus comprises an apparatus body including a housing and a movable member for advancing a needle, the movable member being arranged movably in the housing, and a front end cover attachable to the apparatus body for contacting a portion to be lanced in lancing. The movable member is provided with a first contact portion, whereas the front end cover is provided with a second contact portion for contacting the first contact portion for controlling the movement of the movable member toward the front-end side.

In this structure, the lancing depth of the needle in the portion to be lanced is adjustable by selecting a contact position in the first contact portion or the second contact portion. The lancing depth adjustment mechanism in the present invention can be realized just by providing a first contact portion in the lancet holder of the apparatus body and providing a second contact portion in the front end cover. For example, as noted above, when the lancet holder and the front end cover are formed by resin molding, the first and the second contact portions can be formed just by appropriately designing the configuration of the mold used for the resin molding. In this way, the lancing depth adjustment mechanism can be provided easily with a smaller number of parts as compared with the prior art apparatus.

Preferably, to reliably adjust the lancing depth, one of the first contact portion and the second contact portion may include a plurality of flat contact surfaces which differ from each other in distance from the front end surface of the selected front end cover when the front end cover is attached to the apparatus body. Alternatively, one of the first contact portion and the second contact portion includes a contact surface having a configuration providing a continuously varying distance between the contact surface and the front end surface of the front end cover. However, the first and the second contact surfaces may have any configuration as long as they can contact each other and adjust the lancing depth depending on the contacting portions.

In a preferred embodiment, the front end cover is removably attachable to the apparatus body. The apparatus body is provided with a reference mark, whereas the front end cover is provided with one or a plurality of lancing depth adjustment marks. The lancing depth of the needle in the portion to be lanced is adjustable by selecting an alignment state of the adjustment mark or the adjustment marks with the reference mark in attaching the front end cover to the apparatus body.

This structure is convenient, because the lancing depth is adjustable in attaching the front end cover. The adjustment of the lancing depth can be performed easily just by selecting the alignment state between the reference mark and the adjustment mark.

In a preferred embodiment, the front end cover includes a plurality of projections. The housing includes a guide portion for engaging at least one of the projections to control the movement of the front end cover when the front end cover is attached to the apparatus body with the lancing depth adjustment mark or the lancing depth adjustment marks aligned with the reference mark, and an engagement portion for engaging at least one of the projections when the front end cover is turned circumferentially relative to the housing.

With this structure, the movement path of the projections of the front end cover is defined by the guide portion and the engagement portion, so that the front end cover can be reliably attached to the lancing apparatus body easily. Further, the intended lancing depth can be reliably selected easily.

In a preferred embodiment, at least one of the projections is positioned at the guide portion when the lancing depth adjustment mark or selected one of the lancing depth adjustment marks is aligned with the reference mark.

With this structure, the lancing apparatus can be reliably set to the lancing depth selected by the user.

In a preferred embodiment, the needle is incorporated in the apparatus body as an integral part of a lancet, and the lancet is mounted to the lancet holder in a state in which the front end cover is not attached to the apparatus body.

In this case, the front end cover need be detached from the apparatus body before mounting the lancet and need be attached to the apparatus body after the lancet is mounted. Therefore, when a structure in which the lancing depth is to be adjusted in attaching the front end cover is employed, the selection of the lancing depth is necessary every time the lancet is mounted. In this way, with the structure in which the lancing depth is selected using the occasion of mounting the lancet, the lancing depth can be selected properly in each time of lancing, whereby just a sufficient amount of blood can be extracted without giving unnecessary pain to the user.

In the lancing apparatus of the present invention, the lancing depth of the needle in the portion to be lanced may be kept constant by causing the first contact portion to contact the second contact portion when the movable member is advanced. In such a case, the lancing operation providing stable lancing depth can be performed. The first and the second contact portions may have any configuration as long as they can contact each other.

In a preferred embodiment, the lancing apparatus further comprises suction means for generating negative pressure in the front cover, and the front end cover includes a controlling portion for controlling the degree of bulging of the portion to be lanced when the portion to be lanced is bulged by generating negative pressure in the front end cover by the suction means.

With this structure, the bulging degree of the portion to be lanced during the suction can be made constant regardless of the softness of the portion to be lanced, so that stable lancing operation can be performed.

BRIEF DESCRIPTION OF THE DRAWINGS

FIG. 5A is a sectional view taken along lines Va-Va in FIG. 4, whereas

FIG. 7A is a sectional view taken along lines VIIa-VIIa in FIG. 6, whereas

FIGS. 17A through 17C are perspective views illustrating other examples of projections of the lancet holder.

FIG. 22A is a sectional view illustrating another example of front end cover, whereas FIG. 22B is a sectional view taken along lines XXIIb-XXIIb in FIG. 22A.

FIG. 23 is a longitudinal sectional view illustrating another example of lancing apparatus body in the state before lancing.

BEST MODE FOR CARRYING OUT THE INVENTION

Preferred embodiments of the present invention will be described below in detail with reference to the accompanying drawings.

Figure 1:
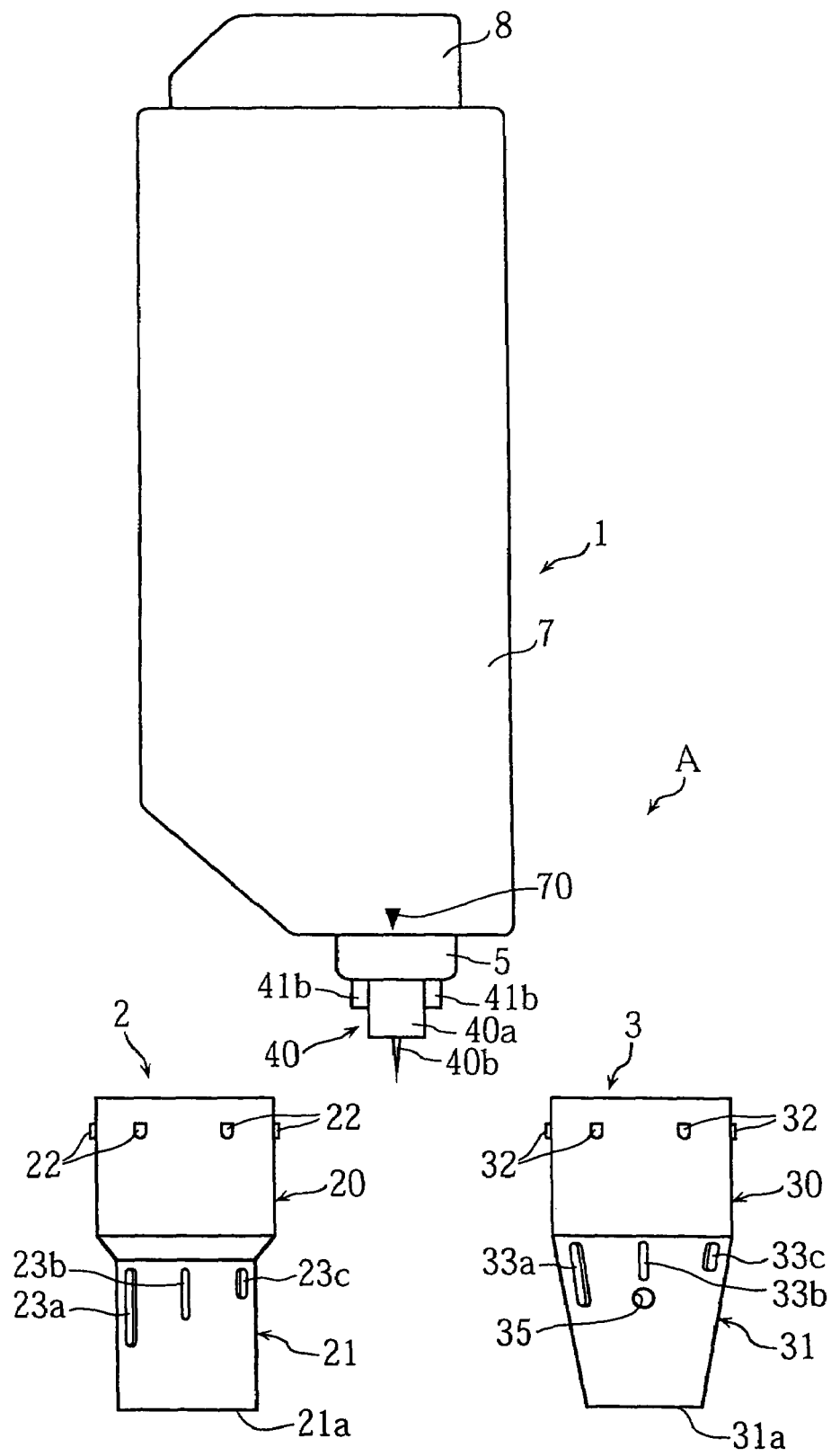
FIG. 1 is a front view illustrating an example of lancing apparatus according to the present invention.

As shown in FIG. 1, the lancing apparatus A in this embodiment includes an apparatus body 1, a lancet 40, a first front end cover 2 and a second front end cover 3. The lancet 40 includes a main body 40a and a needle 40b projecting from the main body. The main body 40a may be made of a synthetic resin, for example. The needle 40b may be made of metal and integrally formed on the main body 40a by insert molding, for example.

Figure 2:
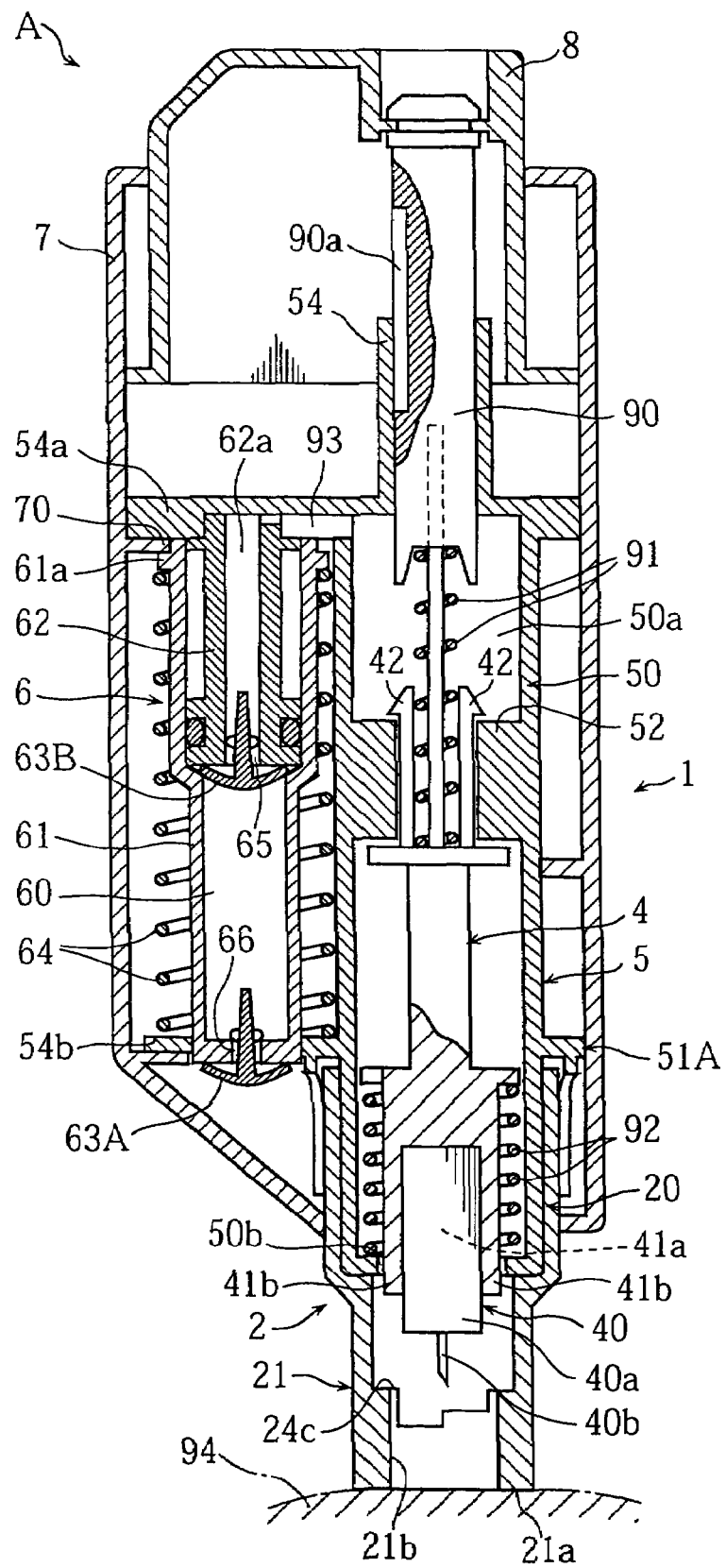
FIG. 2 is a sectional view illustrating the lancing apparatus body of FIG. 1, to which a lancet and a first front end cover are attached.
Figure 3:
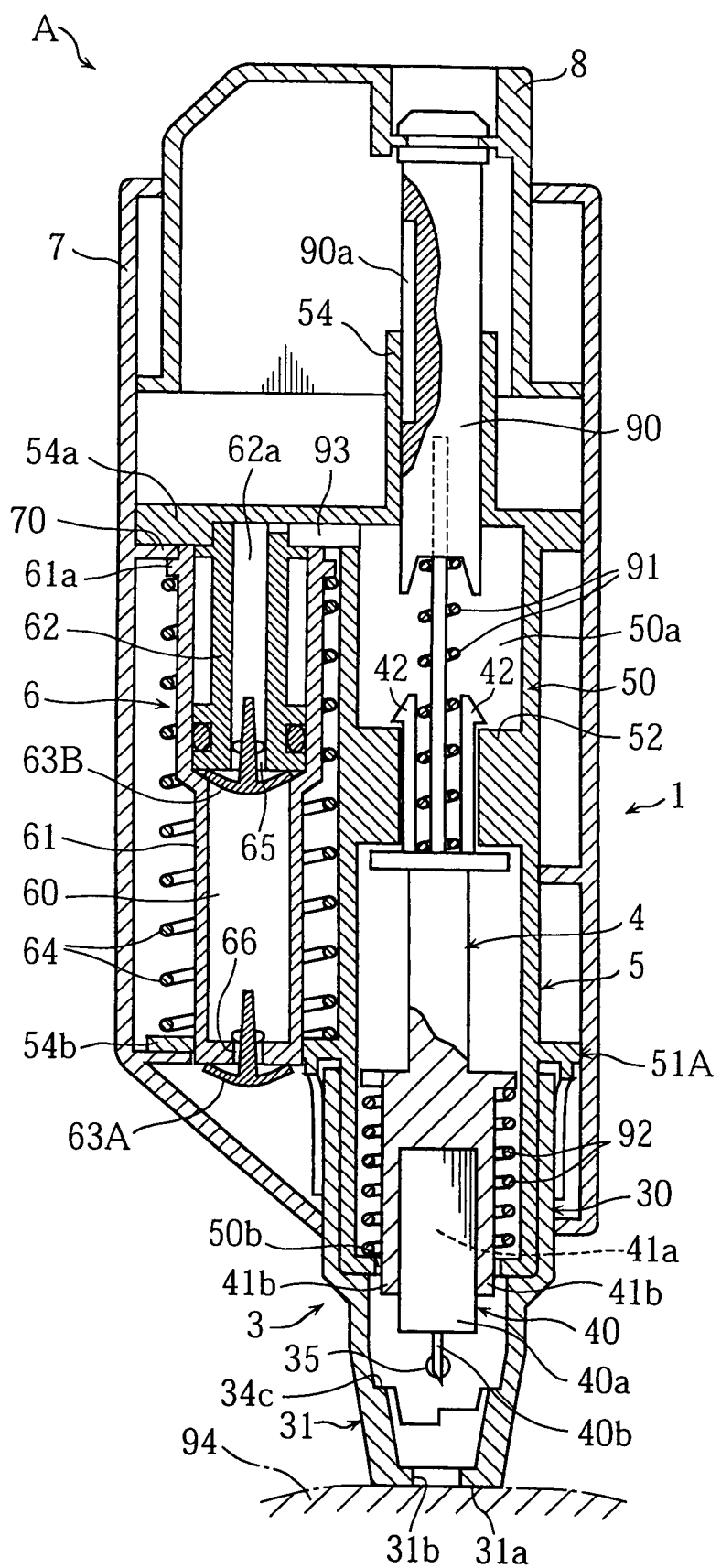
FIG. 3 is a sectional view illustrating the lancing apparatus body of FIG. 1, to which a lancet and a second front end cover are attached.

The first front end cover 2 has a structure for enabling proper blood extraction from a forearm, whereas the second front cover 3 has a structure for enabling proper blood extraction from a fingertip. Thus, the one which is suitable for the portion to be lanced is selected from the front end covers 2 and 3 and attached to the lancing apparatus body 1. FIG. 2 illustrates the state in which the first front end cover 2 is attached, whereas FIG. 3 illustrates the state in which the second front cover 3 is attached. Alternatively, three or more front end covers may be prepared, and one selected from these covers may be attached to the lancing apparatus body 1.

Figure 4:
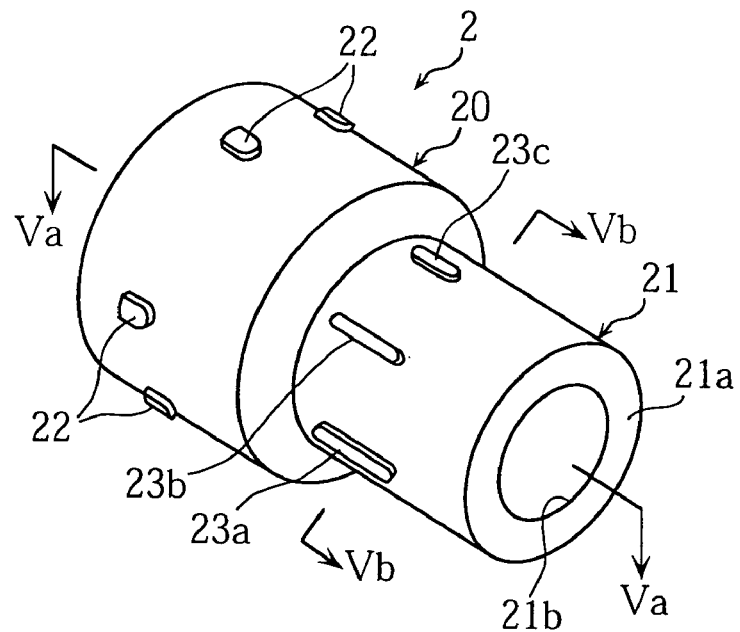
FIG. 4 is a perspective view of the first front end cover.
Figure 5A:
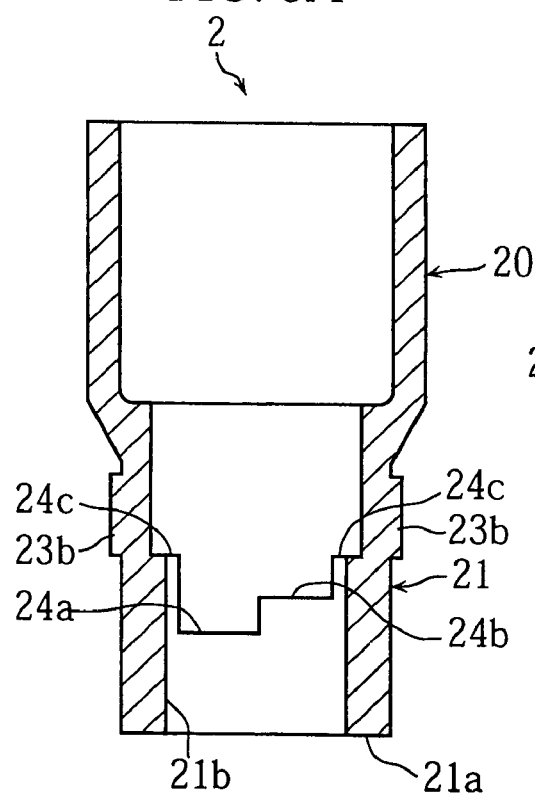
Figure 5B:
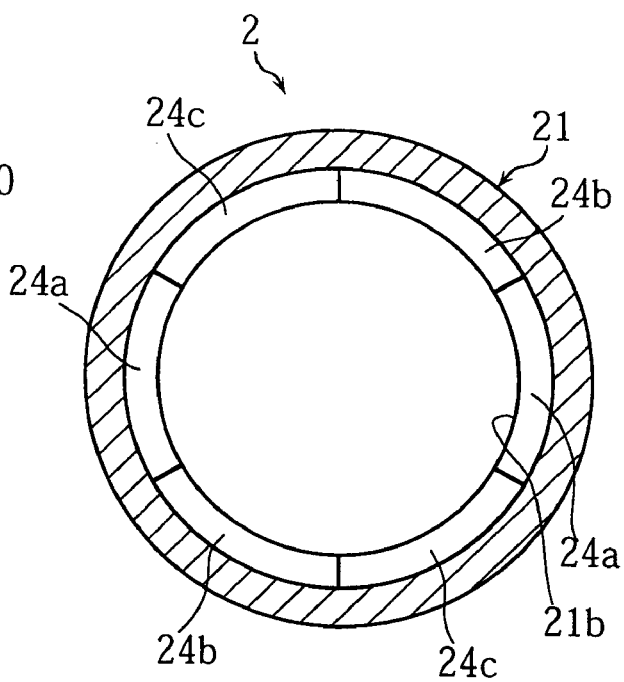
FIG. 5B is a sectional view taken along lines Vb-Vb in FIG. 4.

As shown in FIGS. 4, 5A and 5B, the first front cover 2 has a cylindrical configuration including a larger diameter portion 20 and a smaller diameter portion 21. The larger diameter portion 20 has an outer circumferential surface formed with a plurality of projections 22 arranged at a predetermined pitch. Though not clearly shown in the figure, six projections 22 are provided in this embodiment. By bringing the projections 2 into engagement with a cover attach portion 51 or disengaging the projections from the cover attach portion which will be described later, the first front end cover 2 can be attached to or detached from a housing 5 (See FIG. 9). The smaller diameter portion 21 has an outer circumferential surface formed with a first through a third lancing depth adjustment marks 23a, 23b and 23c. These marks 23a-23c are used for adjusting the lancing depth in attaching the first front end cover 2 to the apparatus body 1. The adjustment marks 23a-23c extend axially of the smaller diameter portion 21 and different from each other in length. The smaller diameter portion 21 has an inner wall provided with first through third contact surfaces 24a, 24b and 24c, which differ from each other in distance from the front end 21a of the smaller diameter portion 21. Specifically, as shown in FIG. 5B, two contact surfaces 24a, two contact surface 24b and two contact surfaces 24c are provided.

The front end of the first front end cover 2 is formed with an opening 21b. Generally, skin of the forearm is soft and unlikely to bleed. Therefore, to extract blood from the forearm, it is preferable to lance the skin in a sucked state or suck the skin after lancing. As will be described later, the lancing apparatus body 1 includes a pump mechanism 6 (See FIGS. 2 and 3). To perform proper sucking of the skin using the pump mechanism 6 for proper bleeding from the forearm, the opening 21b of the first front end cover 2 is made relatively large. For example, the opening 21b may have a diameter of 1 to 3 cm.

Figure 6:
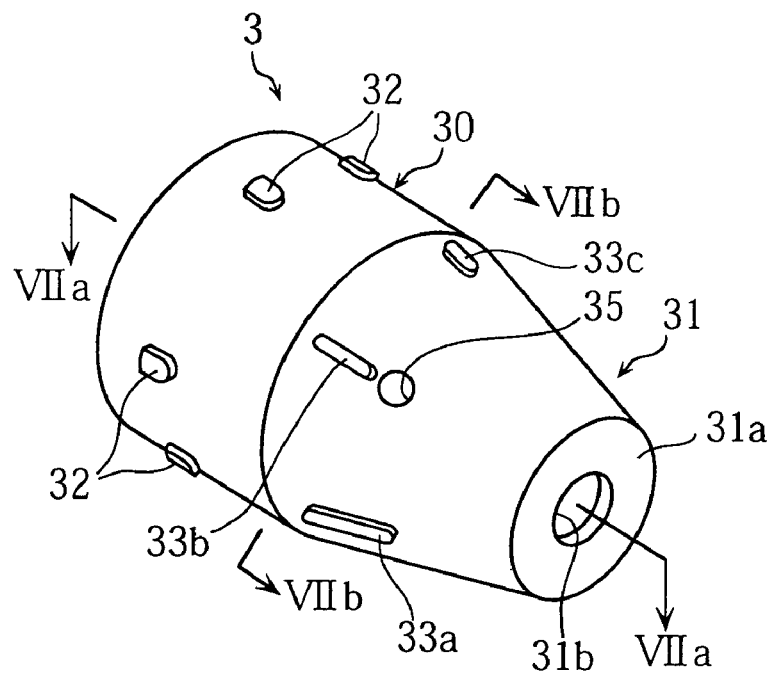
FIG. 6 is a perspective view of the second front end cover.
Figure 7A:
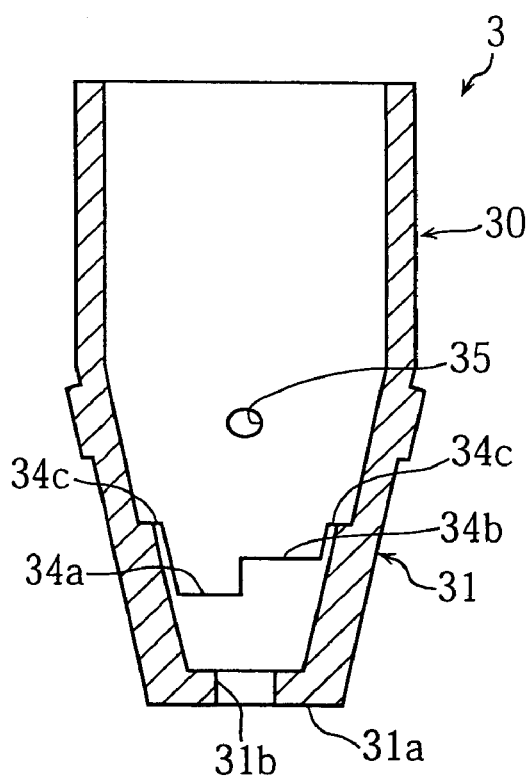
Figure 7B:
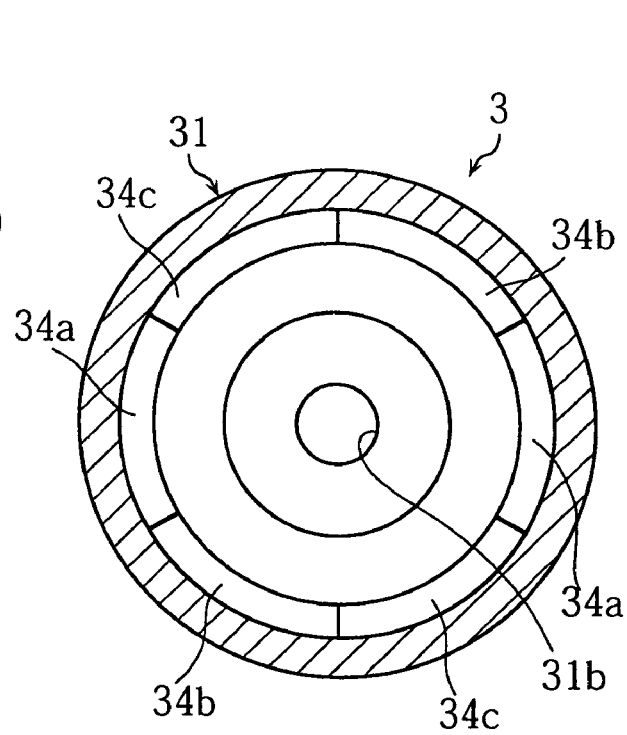
FIG. 7B is a sectional view taken along lines VIIb-VIIb in FIG. 6.

As shown in FIGS. 6, 7A and 7B, the second front cover 3 has a cylindrical configuration including a cylindrical portion 30 and a tapered portion 31. The cylindrical portion 30 has an outer circumferential surface formed with a plurality of projections 32 arrange data predetermined pitch. Though not clearly shown in the figure, six projections 32 are provided in this embodiment. Similarly to the first front end cover 2, the second front end cover 3 can be attached to or detached from the housing 5 by bringing the projections 32 into engagement with the cover attach portion 51 (See FIG. 9) or disengaging the projections from the cover attach portion. The tapered portion 31 has an outer circumferential surface formed with a first through a third lancing depth adjustment marks 33a, 33b and 33c. These marks 33a-33c are used for adjusting the lancing depth in attaching the second front end cover 3 to the lancing apparatus body 1 and different from each other in length. The tapered portion 31 has an inner wall provided with first through third contact surfaces 34a, 34b and 34c, which differ from each other in distance from the front end 31a of the tapered portion 31. As shown in FIG. 7B, two contact surfaces 34a, two contact surface 34b and two contact surfaces 34c are provided. The second front end cover 3 is further formed with a through-hole 35 for providing communication between the inside and outside of the second front end cover 3.

The front end of the second front end cover 3 is formed with an opening 31b. In extracting blood from the fingertip, if the opening 31b is large, the relative height of the skin surface is largely influenced by variations in the softness of skin or the manner of pressing the front end cover against the skin and hence cannot be kept so stable as in extracting blood from the forearm. Further, it is difficult to keep the cover stably in contact with the skin. Therefore, the adjustment of the lancing depth is difficult. On the other hand, unlike the forearm, the fingertip is likely to bleed so that the blood extraction from the fingertip does not require suction of the skin. Therefore, the opening 31b of the second front end cover 3 is made relatively small so that the adjustment of the lancing depth can be performed reliably for proper blood extraction from the fingertip. For example, the opening 31b may have a diameter of 0.2 to 1 cm.

In this way, since selected one of the first front end cover 2 for the forearm and the second front end cover 3 for the fingertip can be removably attached to the apparatus body for use, blood can be extracted from either portion without separately preparing a lancing apparatus for blood extraction from the forearm and that for blood extraction from the fingertip. When the first front end cover 2 having a relatively large opening 21b is used in extracting blood from the forearm, the skin bulges when the front end cover 2 is pressed against the skin 94, whereby the adhesion between the skin and the front end cover 2 is enhanced. Therefore, the formation of a gap between the first front end cover 2 and the skin 94 during the suction is prevented, so that stable suction can be performed. On the other hand, since the opening 31b of the second front end cover 3 is relatively small, when the second front end cover 3 is pressed against the skin 94, variations in the bulging amount of the skin due to the variations of softness of the skin 94 are small. Therefore, the positional relationship between the needle 40b of the lancet 40 and the skin 94 can be made generally constant among the users, so that any user can perform the lancing operation properly.

Figure 8:
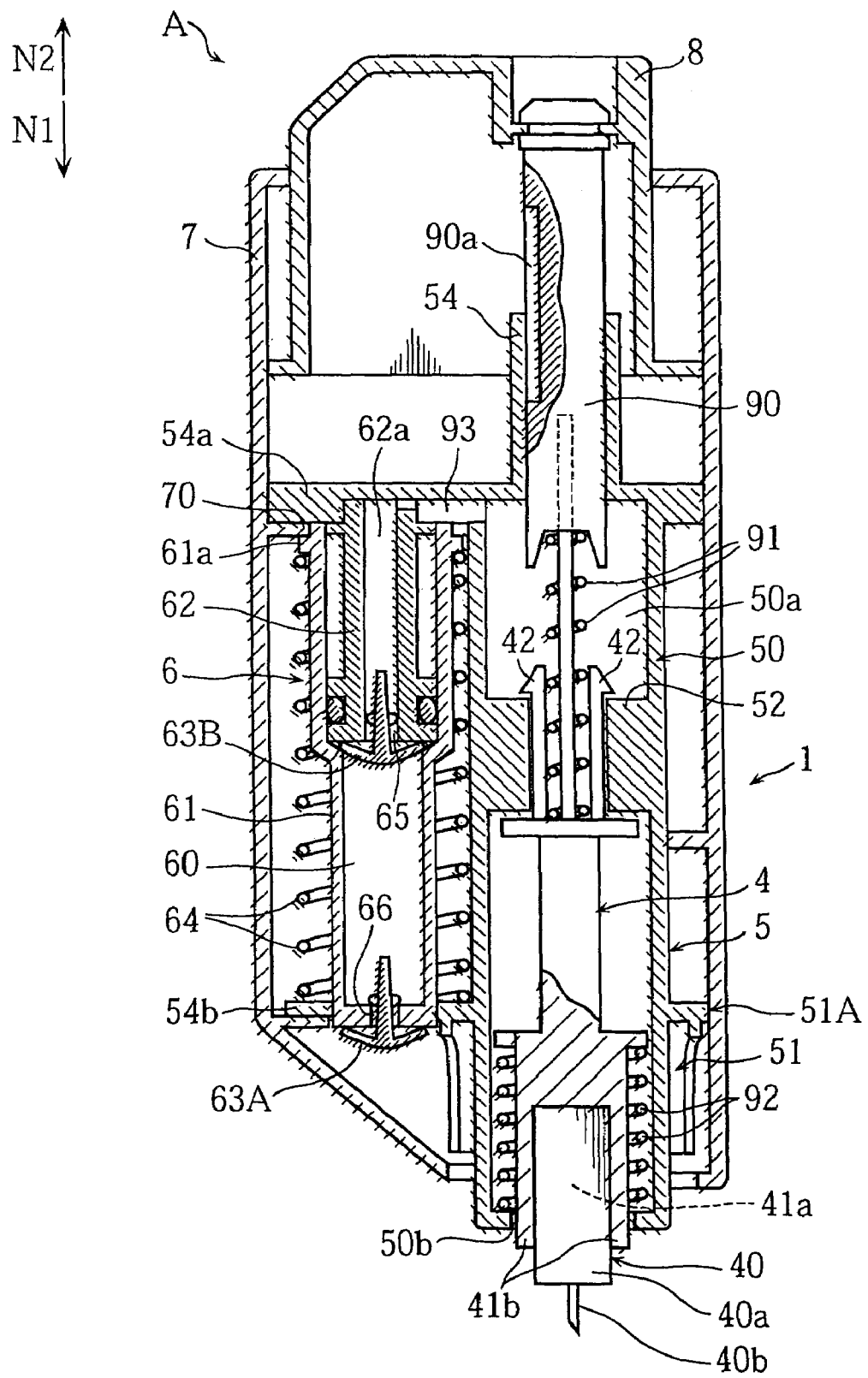
FIG. 8 is a sectional view illustrating the apparatus body of FIG. 1, to which a lancet is attached.

As shown in FIG. 8, the lancing apparatus body 1 is made up of a lancet holder 4 for holding the lancet 40, the housing 5 accommodating the lancet holder 4, the pump mechanism 6, an operation casing 7 for operating the pump mechanism 6, an operation cap 8 for advancing the lancet holder 4 and other parts which will be described later.

The housing 5 is made up of a main body 50 and the cover attach portion 51. The main body 50 has an interiial space 50a for accommodating the lancet holder 40 and allowing the lancet holder to move reciprocally. The cover attach portion 51, to which the front end cover 2 or 3 is to be attached, is provided at the front end of the main body 50. As clearly shown in FIG. 9, the cover attach portion 51 includes a base portion 51A integrally toured on the main body 50, and two engagement pieces 51B and two guide pieces 51C extending from the base portion. The two engagement pieces 51B face each other while interposing the main body 50 therebetween, so do the two guide pieces 51C. The engagement pieces 51B and the guide pieces 51C are spaced from the main body 50. Between each of the engagement pieces 51B and the adjacent one of the guide pieces 51C is provided a recess. In attaching the first or the second front end cover 2 or 3, the projection 22, 32 of the front end cover 2, 3 is positioned at this portion to guide the end cover 2, 3. Each of the engagement pieces 51B is formed with a cutout 51b for engaging the projection 22, 32 of the front end cover 2, 3. The front end cover 2, 3 is attached to the housing 5 by bringing the projection 22, 32 into engagement with the cutout 51b.

The housing 5 may be formed of a single member or by combining a plurality of parts. An O-ring may be attached to the cover attach portion 51 so that the adhesion between the first or the second front end cover 2, 3 and the housing 5 is enhanced when the front end cover 2, 3 is attached to the housing 5. For example, the O-ring may be interposed between the upper end surface of the first or the second front end cover 2, 3 and the base portion 51A of the cover attach portion 51 or between the inner surface of the first or the second front end cover 2, 3 and the outer surface of the housing 5. With this arrangement, enhanced airtightness is provided in the front end cover 2, 3 when the front end cover 2, 3 is brought into contact with the skin. The O-ring may be attached to the front end cover 2, 3. Alternatively, the cover attach portion 51 may be dispensed with, and the first or the second front cover 2, 3 may be rotatably attached to the housing 5 via an O-ring.

The lancet holder 4 is elongate in the direction indicated by arrows N1, N2 in FIG. 8 and advances toward the front end of the housing 5 (in the N1 direction in FIG. 8) when the operation cap 8 is pressed. The lancet holder 4 has a front end 41 formed with a recess 41a and a pair of projections 41b. The recess 41a serves to hold the lancet 40. When the lancet holder 4 is moved toward the front-end side, the paired projections 41b come into selective engagement with the first through the third contact surfaces 24a-24c, 34a-34c of the first or the second front end cover 2, 3. This engagement prevents further advance of the lancet holder 4, whereby the front end position of the needle 40b of the lancet 40 is determined. In this way, the front end position of the needle 40b, i.e., the lancing depth can be adjusted by selecting which of the contact surfaces 24a-24c, 34a-34c to come into engagement with the projections 41b.

Figure 10A:
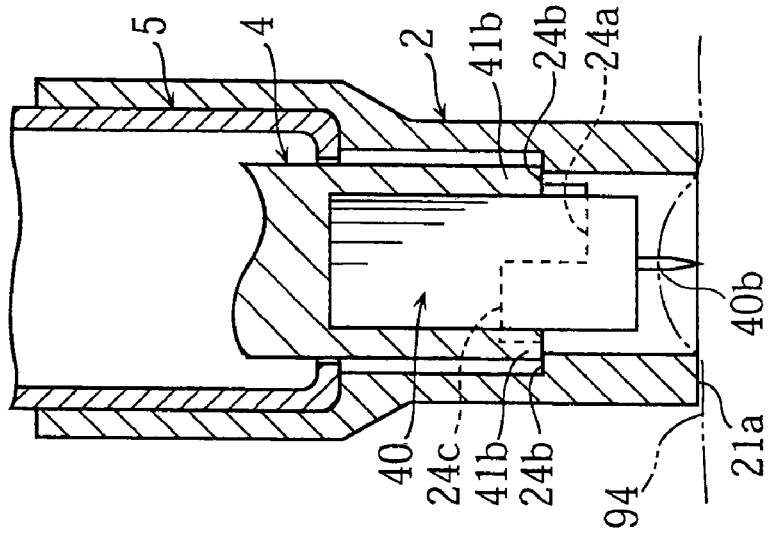
FIGS. 10A through 10C are sectional views illustrating a principal portion for describing the lancing depth adjustment operation.
Figure 10B:
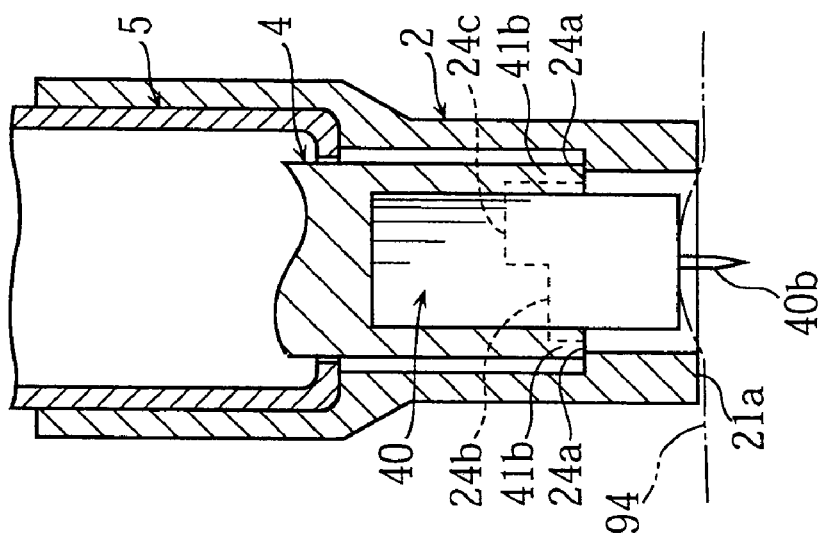
Figure 10C:
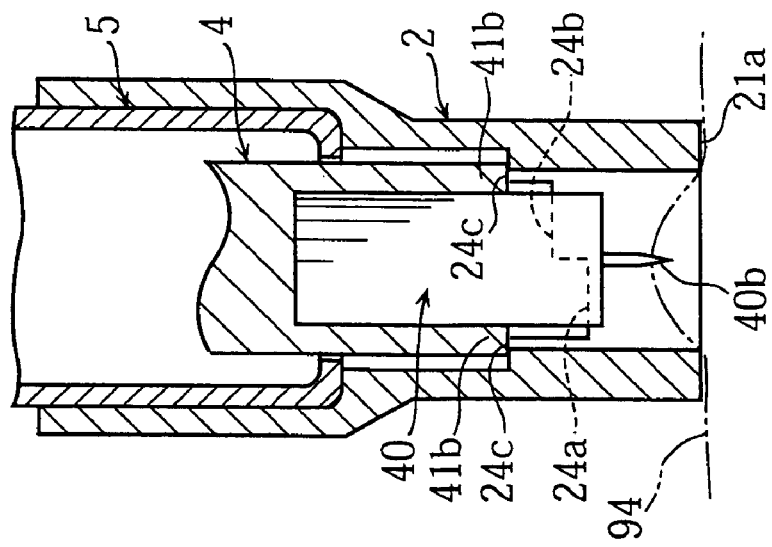

Specifically, in using the first front end cover 2 for example, the insertion depth of the needle 40b in the skin 94 becomes smallest when the projections 41b are brought into engagement with the third contact surfaces 24c as shown in FIG. 10A and largest when the projections 41b are brought into engagement with the first contact surfaces 24a as shown in FIG. 10B. When the projections 41b are brought into engagement with the second contact surfaces 24b as shown in FIG. 10C, the insertion depth of the needle 40b in the skin 94 becomes medium. In attaching the front end cover 2, 3 as will be described later, the user can select which of the contact surfaces 24a-24c, 34a-34c are to be brought into engagement with the projections 41b.

For realizing the advance movement of the lancet holder, any conventionally known means may be utilized. In this embodiment, the means as shown in FIG. 8 is utilized, which will be described below. The lancet holder 4 includes a plurality of latch pawls 42. By bringing the latch pawls 42 into engagement with a stepped portion 52 provided in the housing 5, the lancet holder is latched at a predetermined position in the housing 5. The engagement of the latch pawls 42 with the stepped portion 52 can be performed by pushing the lancet holder 4 from the front end side of the housing 5 toward the base end side.

The operation cap 8 is slidably fitted in the operation casing 7. When the operation cap 8 is pushed in the direction indicated by the arrow N1, a push rod 90 engaging the operation cap 8 advances while compressing a lancet-holder-advancing spring 91 to eventually push the latch pawls 42. When pushed by the push rod 90, the latch pawls 42 are released from the engaged state (latched state) with the stepped portion 52. As a result, the lancet holder 4 advances quickly in the direction of the arrow N1 due to the resilient force of the spring 91. The advance movement of the lancet holder 4 is inhibited when the projections 41b engage the contact surfaces 24a-24c, 34a-34c (See FIGS. 10A-10C). After the projections 41b engage the contact surfaces 24a-24c, 34a-34c, the lancet holder 4 retreats by an appropriate amount due to the resilient force of a spring 92 provided in the housing 5.

Figure 16:
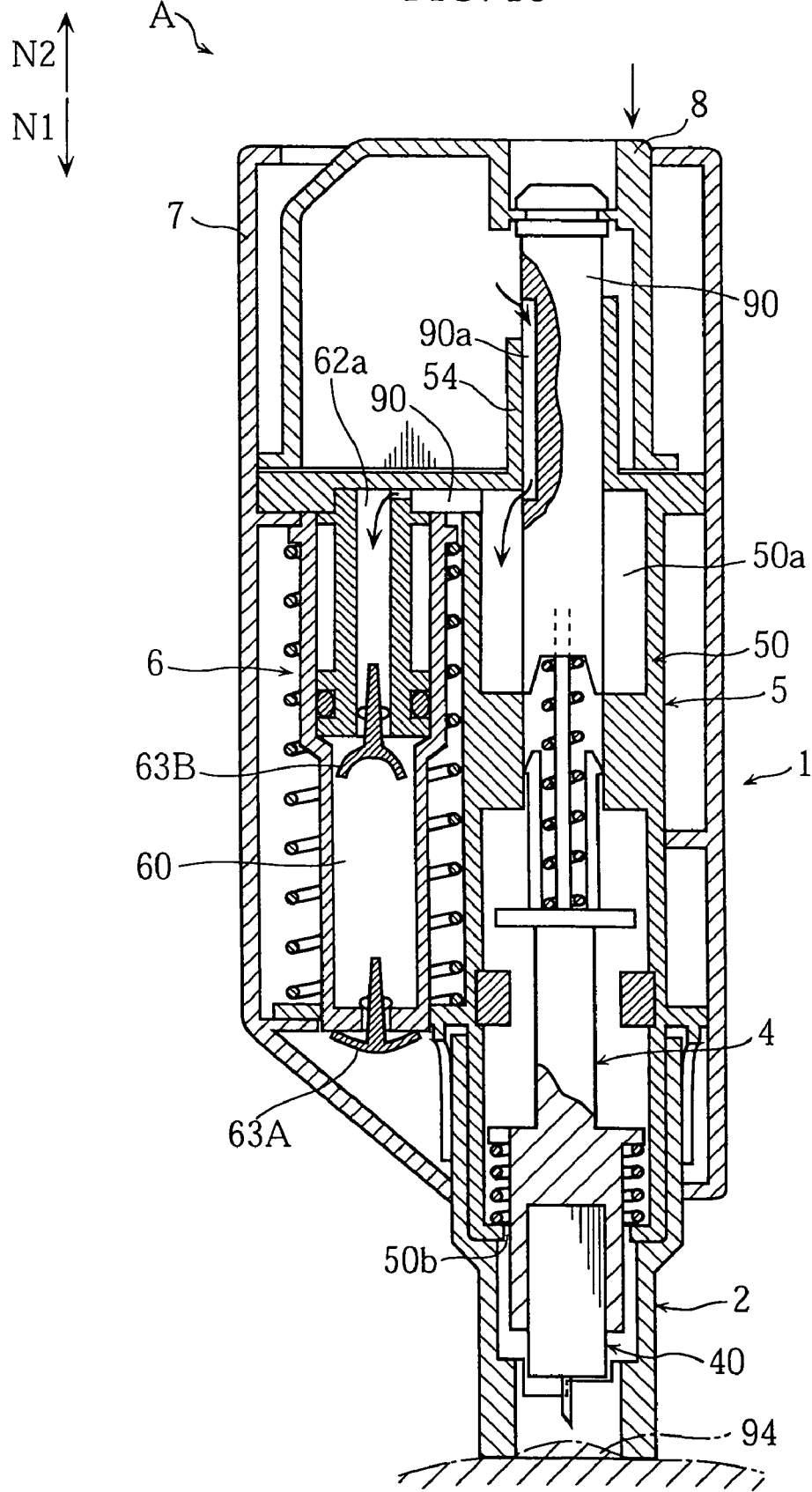
FIG. 16 is a sectional view illustrating the operation for relieving negative pressure in the lancing apparatus shown in FIG. 1.

The push rod 90 has an outer circumferential surface formed with a recess 90a for air passage. Thus, when the push rod 90 advances over a predetermined distance, the internal space 50a of the housing 5 communicates with the outside through the recess 90a. Specifically, the push rod 90 is hermetically fitted in a cylindrical portion 54 provided at the base end of the housing 5 to be slidable in the cylindrical portion, so that normally, communication through the recess 90a is not provided between the internal space 50a of the housing 5 and the outside. However, as shown in FIG. 16, when the operation cap 8 is further pushed by a predetermined amount after the lancet holder 4 is advanced by pushing the operation cap 8, part of the recess 90a is located in the internal space 50a. Therefore, communication through the recess 90a is provided between the internal space 50a and the outside of the housing 5.

Figure 11:
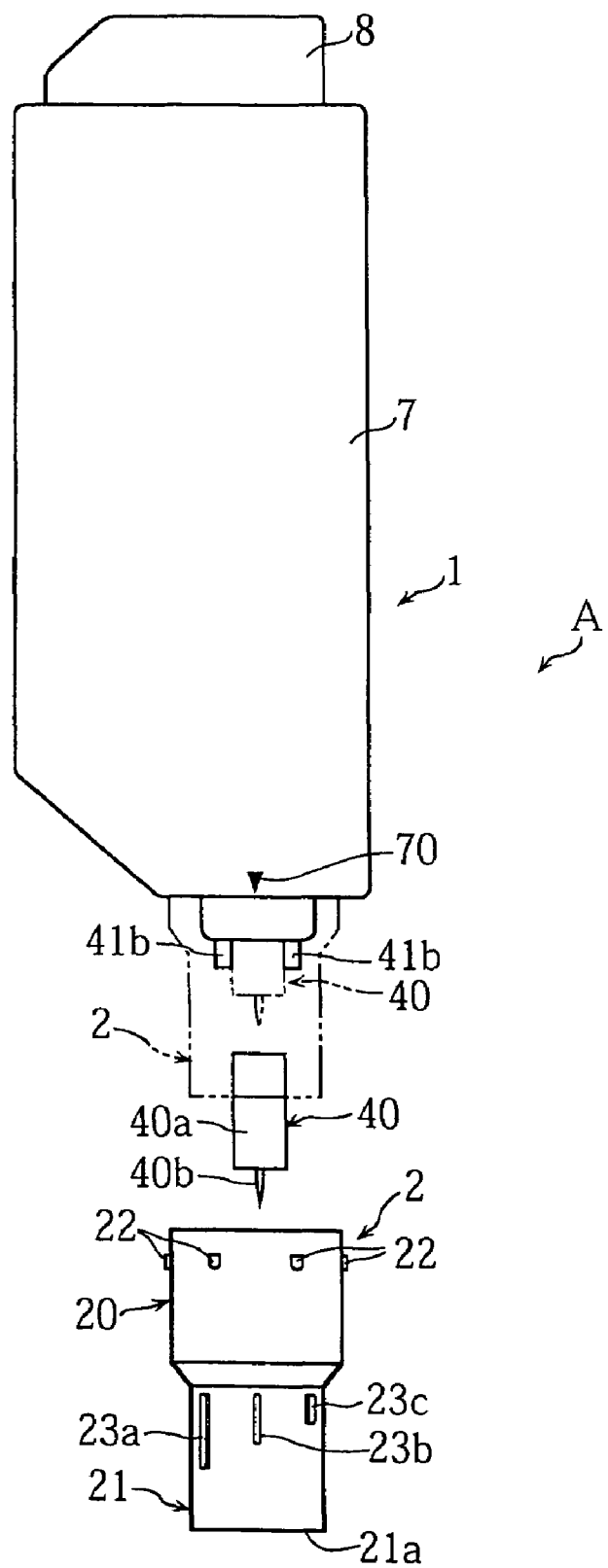
FIG. 11 is a front view for describing the manner of attaching the lancet and the front end cover to the lancing apparatus body of FIG. 1.

The operation casing 7 serves to operate the pump mechanism 6 and has a cylindrical configuration surrounding the housing 5 and the pump mechanism 6. The operation casing 7 is reciprocally movable longitudinally of the housing 5, i.e. in the direction indicated by the arrows N1 and N2. As shown in FIG. 11, the operation casing 7 has an outer surface formed with a reference mark 70. The reference mark 70 is utilized for setting the lancing depth in attaching the first or the second front end cover 2, 3 to the housing 5. Specifically, the lancing depth becomes smallest (See FIG. 10A) when the shortest adjustment mark 23c or 33c is aligned with the reference mark 70, whereas the lancing depth becomes largest (See FIG. 10B) when the longest adjustment mark 23a or 33a is aligned with the reference mark. When the adjustment mark 23b or 33b of the medium length is aligned with the reference mark, the lancing depth becomes the medium (See FIG. 10C).

Figure 13:
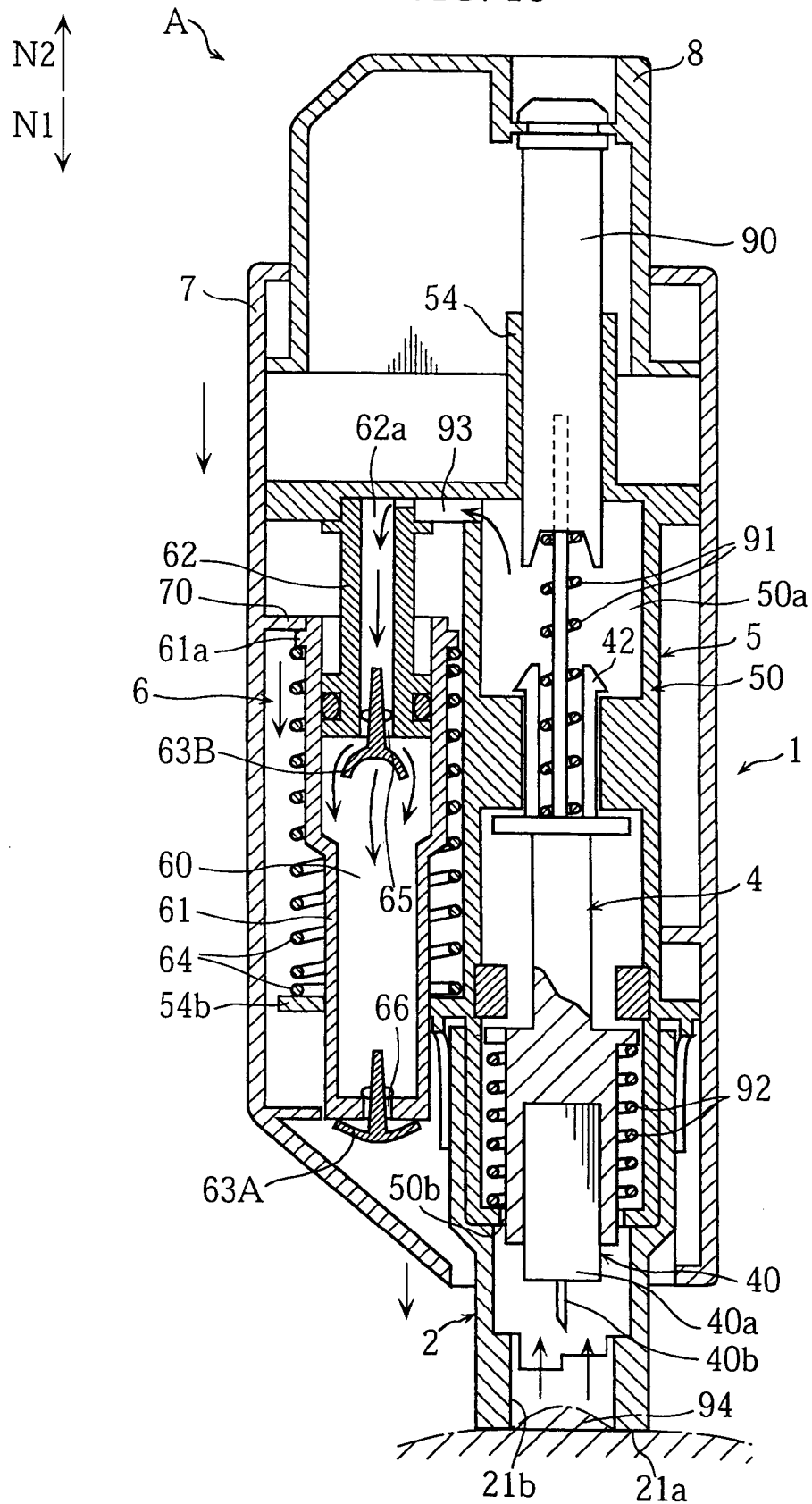
FIG. 13 is a sectional view illustrating the operation for generating negative pressure in the lancing apparatus shown in FIG. 1.

As shown in FIG. 8, the pump mechanism 6 includes a cylinder 61 defining therein a pressure chamber 60, a plunger 62 slidably fitted in the cylinder 61, a first check valve 63A, a second check valve 63B, and a spring 64 for returning. The plunger 62 is fixed to a first support plate 54a projecting from the main body 50 of the housing 5. The cylinder 61 is reciprocally movable relative to the housing 5 and the plunger 62 in the direction indicated by the arrows N1, N2. The cylinder 61 is provided, at the base end thereof (upper portion in the figure), with a flange 61a engaging a projection 70 of the operation casing 7. Thus, as shown in FIG. 13, when the operation casing 7 is moved downward in the direction of the arrow N1, the cylinder 61 also moves downward to increase the capacity of the pressure chamber 60.

As shown in FIG. 8, the spring 64 for returning, which may be a compression spring, is interposed between a second support plate 54b projecting from the main body 50 of the housing 5 and the flange 61a of the cylinder 61. When the cylinder 61 moves downward in the direction of the arrow N1 following the movement of the operation casing 7, the spring 64 is compressed between the flange 61a and the second support plate 54b to produce a resilient force to move the cylinder 61 and the operation casing 7 upward.

The first check valve 63A serves to open or close an air outlet 66 formed at the front end of the cylinder 61. The first check valve allows the air discharge from within the pressure chamber 60 to the outside of the pressure chamber 60 through the air outlet 66 but prevents the air flow in the reverse direction. The plunger 62 is hollow and has a through-hole 62a. The plunger 62 has a front end formed with an air inlet 65. The second check valve 63B serves to open or close the air inlet 65. The second check valve allows air to flow into the pressure chamber 60 through the through-hole 62a of the plunger 62, but prevents the air flow in the reverse direction. The through-hole 62a communicates with the internal space 50a in the housing 5 via an air path 93 formed between the base end of the plunger 62 and the first support plate 54 of the housing 5. The internal space 50a is so designed as to provide communication between a portion adjacent the air path 93 and the front end opening 50b of the housing 5. Therefore, when a negative pressure is produced in the pressure chamber 60 of the pump mechanism 6, the negative pressure is exerted onto the front end opening 50b of the housing 5 and hence onto the inside of the front end cover 2, 3.

The usage and advantages of the lancing apparatus A will be described below.

Figure 9:
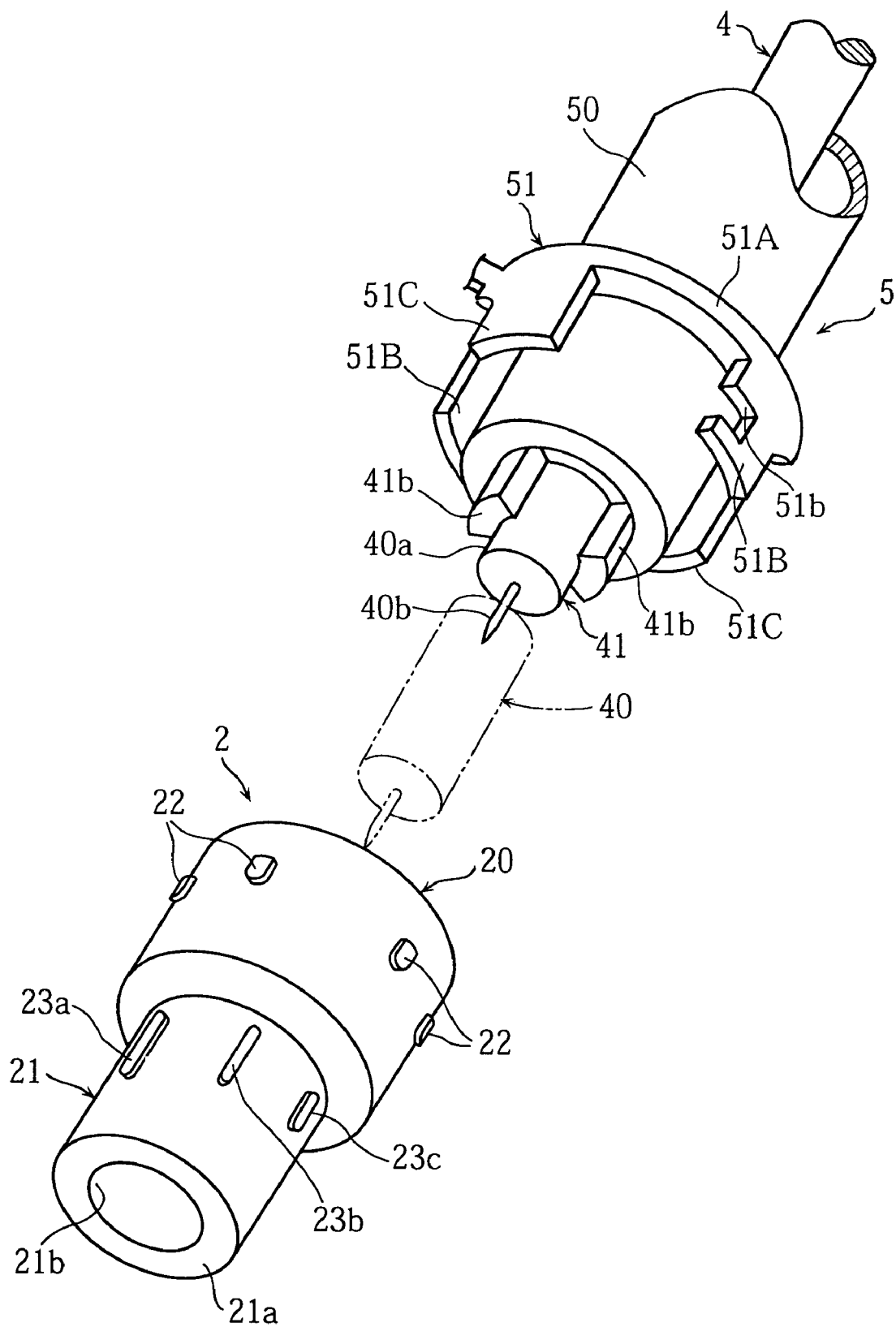
FIG. 9 is a perspective view illustrating a principal portion for describing the manner for attaching the lancet and the front end cover.
Figure 12:
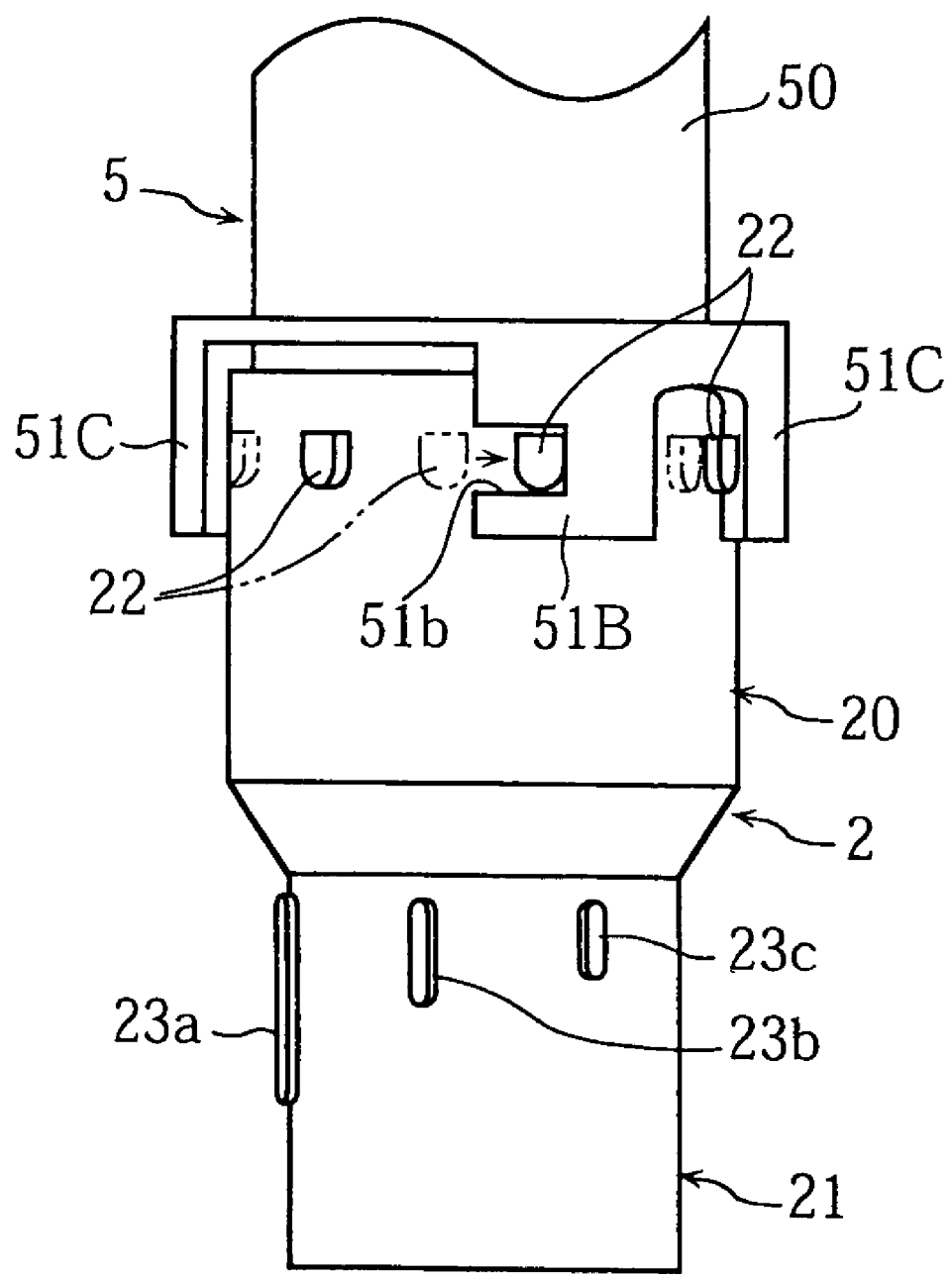
FIG. 12 is a front view illustrating a principal portion for describing the manner of attaching the front end cover to the housing.

To perform the lancing operation, after the lancet 40 is mounted to the lancet holder 4, selected one of the first and the second front end covers 2, 3 is attached, as shown in FIGS. 9, 11 and 12. Preferably, the first front end cover 2 is selected in extracting blood from the forearm, whereas the second front end cover 3 is selected in extracting blood from the fingertip. FIGS. 9, 11 and 12 show an example in which the first front end cover 2 is to be attached, and hereinafter, description will be made mainly as to this example.

The mounting of the lancet 40 is performed by fitting the main body 40a of the lancet 40 into the recess 41a (See FIG. 2) from the side opposite to the needle 40b. At this time, the latch pawls 42 of the lancet holder 4 may be brought into engagement with the stepped portion 52 of the housing 5 to provide the latched state. Alternatively, the latching operation may be provided separately from the operation for mounting the lancet 40. Specifically, the latched state may be provided before the lancet 40 is mounted. The attachment of the first front end cover 2 is performed by three process steps, i.e. the setting of the lancing depth, the provisional attachment of the first front end cover 2 and the fixation of the first front end cover 2.

The setting of the lancing depth is performed by aligning the adjustment mark 23a-23c corresponding to the lancing depth intended by the user with the reference mark 70. As shown in FIG. 12, the provisional attachment of the first front end cover 2 is performed by fitting the first front end cover 2 around the front end of the lancet holder 4 with the selected adjustment mark 23a-23c aligned with the reference mark. In this aligned state, the projections 22 of the first front end cover 2 are positioned in the recess between the engagement piece 51B and the guide piece 51C, as indicated by phantom lines in the figure. When none of the adjustment marks 23a-23c is aligned with the reference mark 70, the projections 22 cannot be positioned in the recess so that the provisional attachment of the first front end cover 2 to the lancet holder 4 cannot be performed. The subsequent fixation of the first front end cover 2 is performed by turning the first front end cover 2 fitted around the front end of the lancet holder 4 in the circumferential direction, as shown in FIG. 12. By the turning of the first front end cover 2, the projection 22 positioned in the recess fits into the cutout 51b. As a result, the front end cover 2 is fixed to the housing 5, thereby realizing the state as shown in FIG. 2. FIG. 2 illustrates an example in which the adjustment mark 23c is aligned with the reference mark 70. In this case, the projections 41b of the lancet holder 4 are located directly above the third contact surfaces 24c so that the projections 41b come into contact with the third contact surfaces 24c when the lancet holder is moved toward the front-end side.

Similarly to the first front end cover 2, the second front end cover 3 is provided with projections 32 and adjustment marks 33a-33c, as clearly shown in FIGS. 6, 7A and 7B. Therefore, the attachment of the second front cover 3 to the housing 5 can be performed similarly to the attachment of the first front end cover 2. FIG. 3 illustrates the state in which the second front end cover 3 is attached to the housing 5. Specifically, this figure exemplarily illustrates the state in which the adjustment mark 33c is aligned with the reference mark 70.

Subsequently, the lancing operation is performed. In extracting blood from the forearm using the first front end cover 2, it is preferable to apply negative pressure to the skin 94 before lancing the skin. In extracting blood from the fingertip using the second front end cover 3, it is not necessary to purposely apply negative pressure on the skin 94, because the fingertip is likely to bleed.

To apply negative pressure to the skin 94, with the front end of the first front end cover 2 pressed against the skin 94, the operation casing 7 is pushed downward in the direction of the arrow N1 for movement relative to the first front end cover 2 and the housing 5, as shown in FIG. 13. This operation causes the cylinder 61 to move downward relative to the plunger 62, thereby increasing the capacity of the pressure chamber 60. Therefore, the interior of the pressure chamber 60 undergoes a pressure drop, and the second check valve 63B opens. As a result, the air flows from the internal space 50a of the housing 5 into the pressure chamber 60 through the air path 93 and the through-hole 62a. Therefore, negative pressure is generated in the first front end cover 2, which can be applied to the skin 94.

Figure 14:
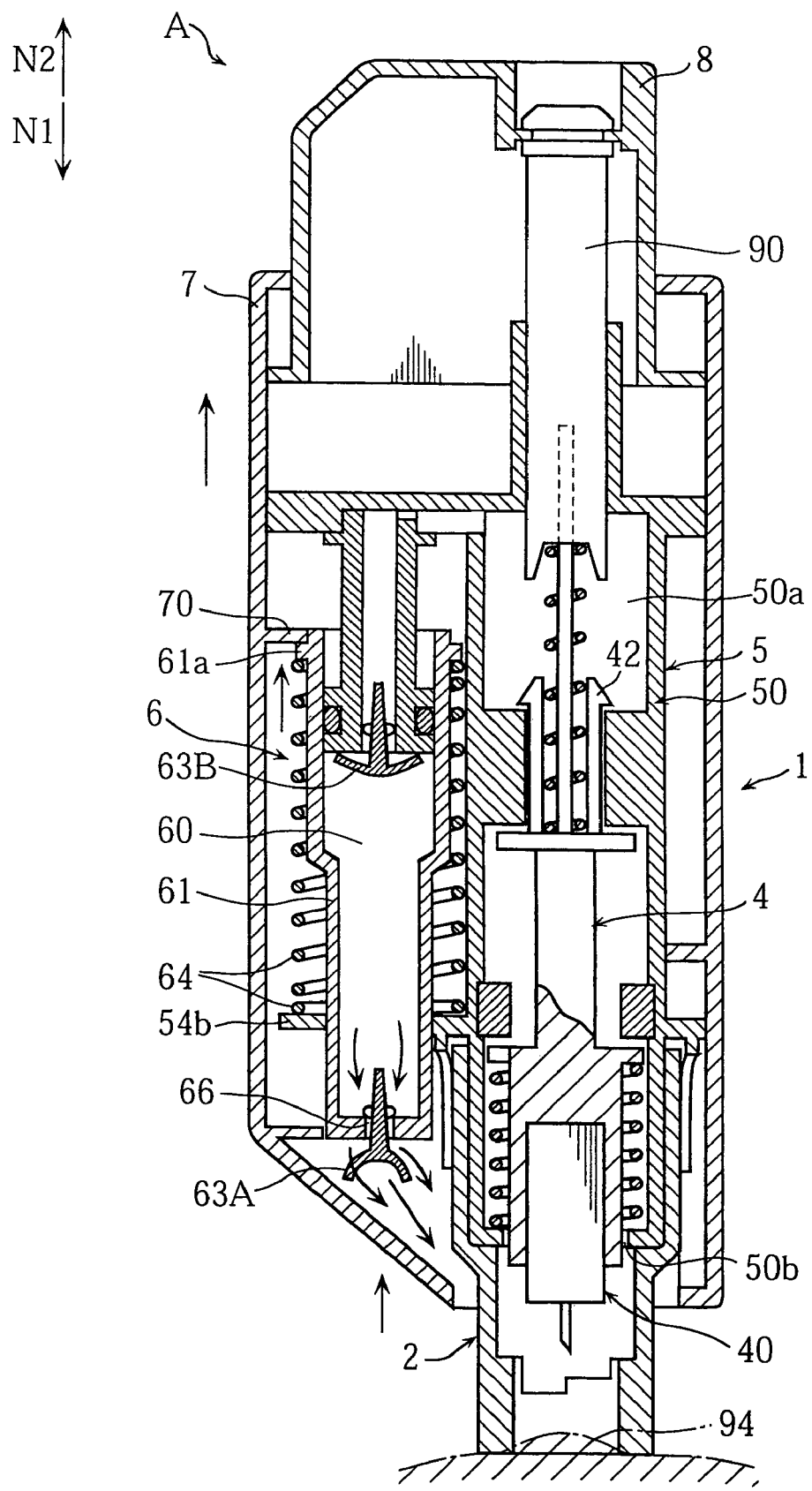
FIG. 14 is a sectional view illustrating the operation for generating negative pressure in the lancing apparatus shown in FIG. 1.

After the operation casing 7 is pushed downward, the operation casing 7 and the cylinder 61 can be easily returned to the original position by utilizing the resilient force of the spring 64. As shown in FIG. 14, when the operation casing 7 and the cylinder 61 return upward in the direction of the arrow N2, the capacity of the pressure chamber 60 reduces. Therefore, the second check valve 63B closes, whereas the first check valve 63A opens. Therefore, when the cylinder 61 returns to the original position, the air in the pressure chamber 60 can be properly discharged to the outside through the air outlet 66 while maintaining the internal space 50a of the housing 5 under negative pressure.

In this way, the internal space 50a of the housing 5 can be maintained under negative pressure in returning the operation casing 7 and the cylinder 61 to the original position. Therefore, when the operation casing 7 is pushed downward again thereafter, the internal space 50a of the housing 5 further undergoes a pressure drop, thereby increasing the negative pressure (lower the absolute pressure) in the internal space 50a. Therefore, in the lancing apparatus A, negative pressure to be applied to the skin 94 can be adjusted appropriately by increasing or decreasing the number of times of the reciprocal movement of the operation casing 7. When negative pressure is not duly generated due to the insufficient adhesion of the first front end cover 2 to the skin 94 or when airtightness is lost after negative pressure is generated, intended negative pressure can be generated by moving the operation casing 7 again. Therefore, excessive bleeding or insufficient bleeding from the skin 94 can be prevented.

As noted above, in extracting blood from the fingertip using the second front end cover 3, negative pressure need not be applied to the skin 94. However, the user may erroneously move the operation casing 7 upward or downward. Even in such a case, since the second front end cover 3 is formed with the through-hole 35 as shown in FIGS. 6 and 7A, air flows from the outside into the front end cover 3 through the through-hole 35. Therefore, negative pressure is not generated in the second front end cover 3.

Figure 15:
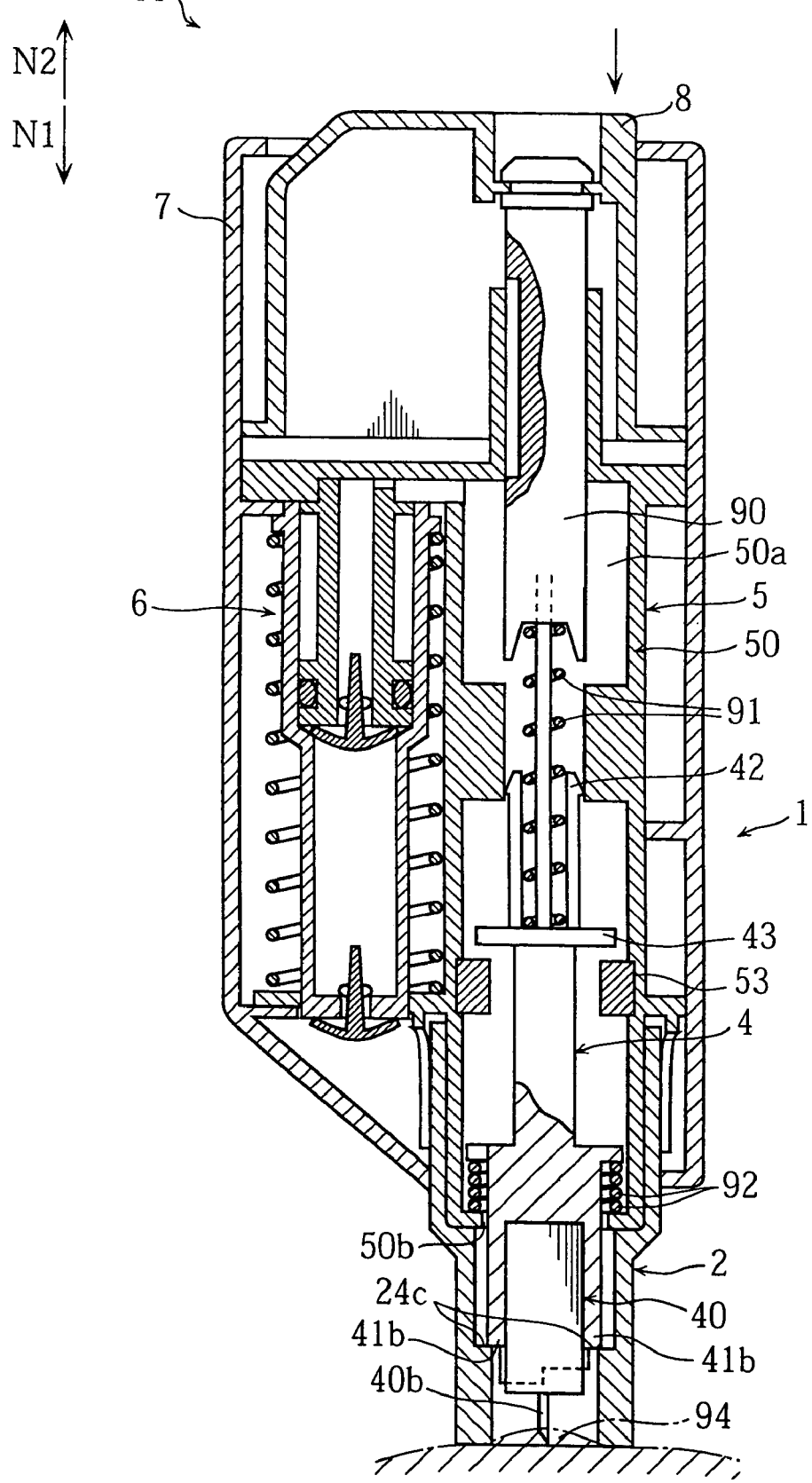
FIG. 15 is a sectional view illustrating the lancing operation of the lancing apparatus shown in FIG. 1.

Subsequently, to lance the skin with the lancet 40, the operation cap 8 is pushed downward in the direction of the arrow N1 to release the latched state of the lancet holder 4, as shown in FIG. 15. As a result, the lancet holder 4 advances due to the resilient force of the spring 91 so that the lancet 40 lances the skin 94. At this time, the projections 41*b* come into contact with the contact surfaces 24*a*, 24*b* or 24*c* corresponding to the lancing depth selected by the user, so that the lancing amount of the needle 40*b* into the skin 94 is controlled. In the example shown in this figure, the projections 41*b* are brought into contact with the third contact surfaces 24*c*. After the lancet 40 sticks in the skin 94, the lancet holder 4 retreats due to the resilient force of the spring 92, so that the lancet 40 is immediately pulled out from the skin 94. Since the negative pressure previously generated is applied to the skin 94, bleeding from the portion lanced by the lancet 40 is promoted.

As shown in FIG. 16, when the operation cap 8 is further pushed downward in the direction of the arrow N1, the internal space 50*a* of the housing 5 communicates with the outside through the recess 90*a* of the push rod 90, and air flows into the internal space 50*a* through the recess 90*a*. As a result, the internal space 50*a* returns to the atmospheric pressure. In this state, the first front end cover 2 can be easily removed from the skin 94.

In the lancing apparatus A, the negative pressure applied to the skin 94 cannot be relieved unless the operation cap 8 is further pushed after the skin 94 is lanced with the lancet 40 by the operation of the operation cap 8. Thus, since the negative pressure applied to the skin 94 is not relieved erroneously before the lancet 40 sticks in the skin, the lancing of the skin can be performed with the skin 94 bulged and good blood circulation maintained. Moreover, both of the sticking of the lancet 40 and the relieving of negative pressure can be successively performed easily by pushing the operation cap 8.

The lancing depth adjustment function of the lancing apparatus A is realized just by providing projections 41*b* in the lancet holder 4 of the lancing apparatus body 1 and providing contact surfaces 24*a*-24*c*, 34*a*-34*c* in the first and the second front end covers 2, 3. The lancing apparatus body 1 and the front end covers 2, 3 are necessary for making the lancing apparatus even when the lancing depth adjustment function is not to be provided. The lancing depth adjustment function of the lancing apparatus A can be provided just by changing the configuration of these parts. For example, when the lancet holder 4 and the first and the second front end covers 2, 3 are formed by resin molding, the projections 41*b* and the contact surfaces 24*a*-24*c*, 34*a*-34*c* can be formed just by appropriately designing the configuration of the mold used for the resin molding. In this way, in the lancing apparatus A, the lancing depth adjustment function can be provided easily without increasing the number of parts of the apparatus, which is advantageous in terms of the manufacturing cost.

In the lancing apparatus A, the first or the second front end cover 2, 3 need be detached from the apparatus body 1 before mounting the lancet 40 and attached to the apparatus body 1 after the lancet 40 is mounted. Therefore, the necessity for selecting the lancing depth occurs every time the lancet 40 is to be mounted. This structure in which the lancing depth is to be selected on the occasion of mounting the lancet 40 prevents the user from forgetting to perform the lancing depth adjustment. Therefore, the apparatus is set to an appropriate lancing depth every time the lancing operation is to be performed, so that just a sufficient amount of blood can be extracted without giving unnecessary pain to the user. Moreover, in addition to the convenience provided by the adjustment of the lancing depth in attaching the first or the second front end cover 2 or 3, the adjustment of the lancing depth can be performed by the easy operation of aligning the reference mark 70 with adjustment marks 23*a*-23*c*, 33*a*-33*c*, which also provides convenience.

In the above-described examples, the skin 94 is lanced with the lancet 40 after negative pressure is generated in the internal space 50*a* of the housing 5. However, with the lancing apparatus A, these operations may be performed in the reverse order. Specifically, the skin may be lanced with the lancet 40 by pushing the operation cap 8, and then negative pressure may be applied to the portion lanced by the lancet 40 by operating the operation casing 7. In the lancing apparatus A, the front end of the first or the second front end cover 2 or 3 massages the skin 94 when the operation casing 7 is moved reciprocally for generating negative pressure, so that the blood circulation in the skin 94 is further promoted.

In the lancing apparatus A, negative pressure is generated when the operation casing 7 is pushed downward. Alternatively, the apparatus may be so structured that negative pressure is generated when the operation casing 7 retreats or by using an electric motor. Since negative pressure need not necessarily be generated in the first or the second front end cover 2, 3, the pump mechanism or the electric pump may be dispensed with.

The present invention is not limited to the foregoing embodiments. Specific structure of each part of the lancing apparatus of the present invention may be modified in various ways. For example, as shown in FIG. 17A, the lancet holder 4 may be provided with a single projection 41*b* or no less than three projections depending on the number or size of the contact surfaces. As shown in FIGS. 17B and 17C, the projection 41*b'* may project radially of the lancet holder 4.

Figure 18:
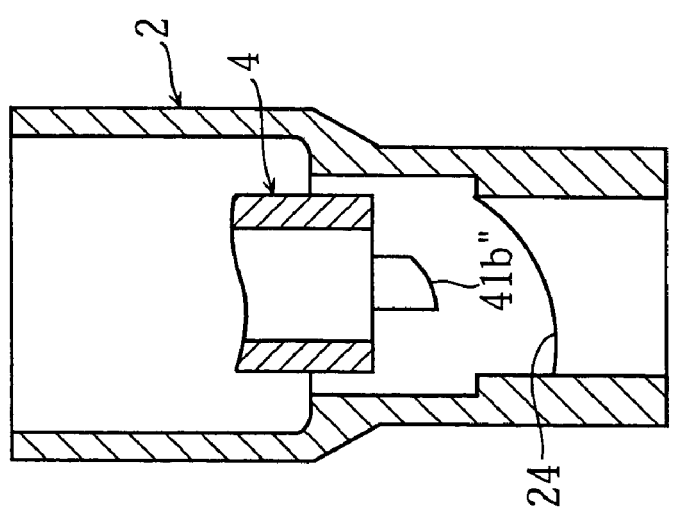
FIG. 18 is a sectional view showing a principal portion of another structure for adjusting the lancing depth.

As shown in FIG. 18, the first front end cover 2 may be formed with a sloping contact surface 24 instead of the first through the third flat contact surfaces 24*a*-24*c* (See FIG. 5A). In this case, it is preferable that the projection 41*b''* has a configuration corresponding to the contact surface 24. Similarly, the second front cover 3 may be formed with a sloping contact surface instead of the first through the third flat contact surfaces 34*a*-34*c* (See FIG. 7A).

Figure 19B:
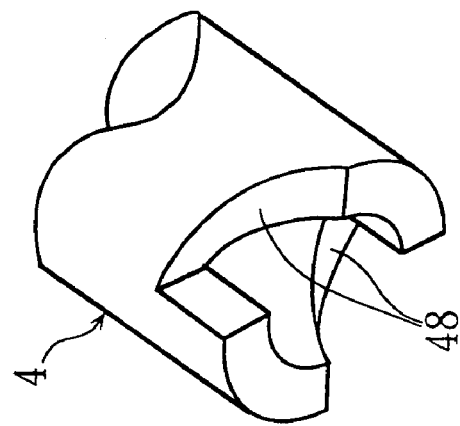
FIGS. 19A and 19B each is a perspective view illustrating a front end of a lancet holder for another lancing depth adjustment structure.
Figure 19A:
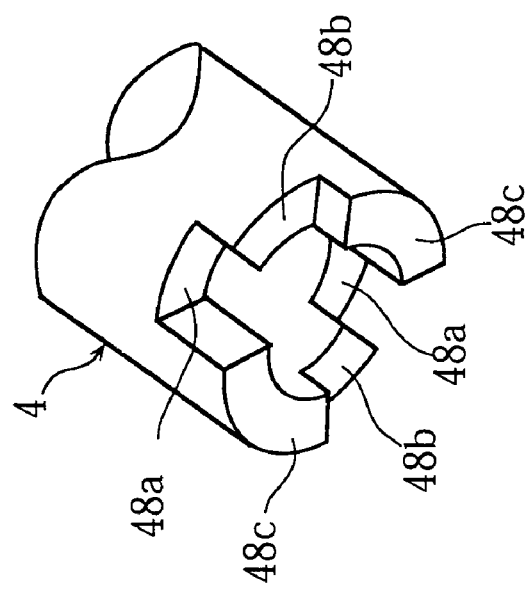
Figure 20A:
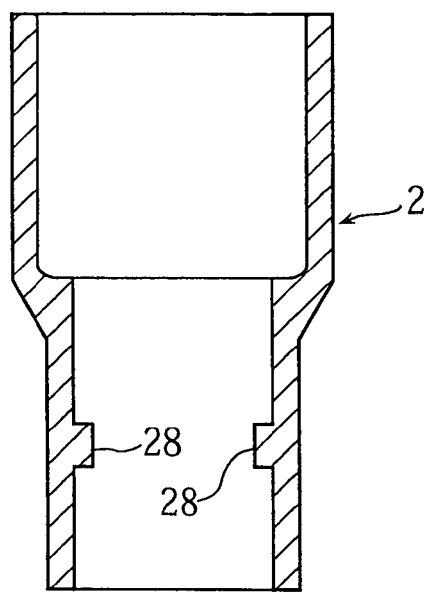
FIGS. 20A and 20B each is a sectional view illustrating a front end cover for another lancing depth adjustment structure.
Figure 20B:
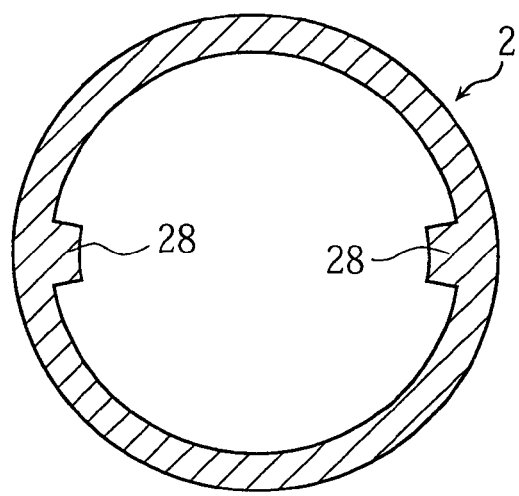

For the adjustment of the lancing depth, the front end of the lancet holder 4 may be formed with contact surfaces 48*a*-48*c* or 48 as shown in FIGS. 19A and 19B, whereas the inner wall of the first front end cover 2 may be formed with projections 28 extending radially inwardly as shown in FIGS. 20A and 20B. In this case, the second front end cover 3 need be formed with similar projections, though not illustrated in the figure.

Figure 21A:
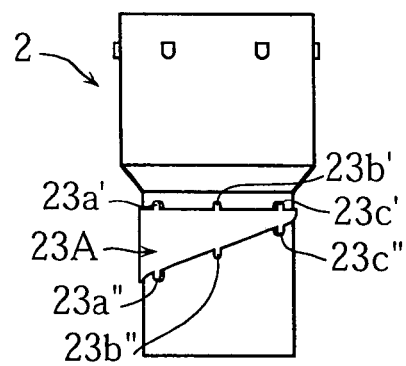
FIGS. 21A through 21D each is a front view illustrating another example of lancing depth adjustment mark provided at a front end cover.
Figure 21B:
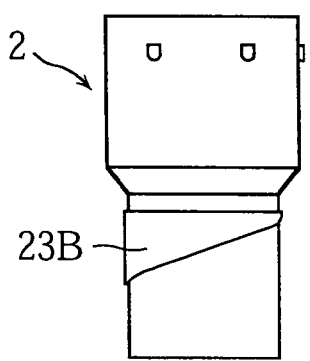
Figure 21C:
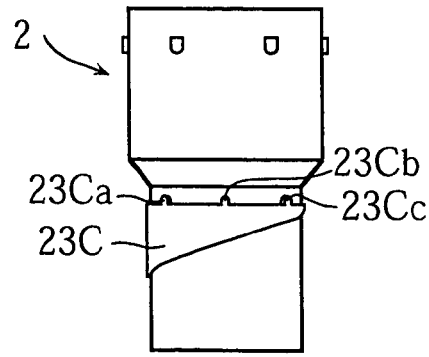
Figure 21D:
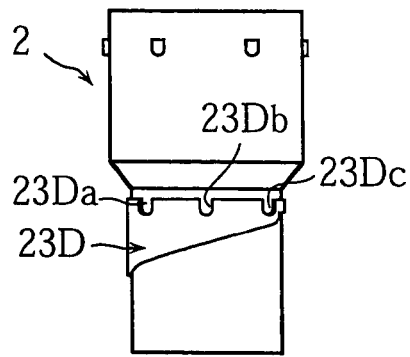

As shown in FIGS. 21A-21D, only a single lancing depth adjustment mark may be provided. Specifically, FIG. 21A illustrates an adjustment mark 23A whose dimension in the axial direction of the first front end cover 2 changes continuously. This adjustment mark is provided with a plurality of projections 23*a'*, 23*b'*, 23*c'*, 23*a''*, 23*b''* and 23*c''* spaced from each other. The projections 23*a'*-23*c'* and 23*a''*-23*c''* of the adjustment mark 23A function similarly to the ends of the adjustment marks 23*a*-23*c* (See FIGS. 1 and 4). Thus, the lancing depth can be adjusted by attaching the first front end cover 2 while aligning the projections 23a'-23c', 23a"-23c" with the reference mark 70 (See FIG. 1). FIG. 21B illustrates an adjustment mark 23B whose dimension in the axial direction of the first front end cover 2 varies continuously. The adjustment mark 23B is suitable for such a structure as shown in FIG. 18, in which a sloping contact surface is provided for realizing stepless adjustment of the lancing depth. For example, when the dimension of the adjustment mark 23B in the axial direction is made proportional to the lancing depth, the user can adjust the lancing depth as desired by aligning the reference mark 70 (See FIG. 1) with a dimensional position corresponding to an intended lancing depth in attaching the first front end cover 2. As shown in FIG. 21C, an adjustment mark 23C formed with projections 23Ca, 23Cb and 23Cc only at one edge thereof may be employed. Alternatively, instead of the projections, the adjustment mark may be formed with recesses 23Da, 23Db, 23Dc, as shown in FIG. 21D. The configuration of the adjustment mark is not limited to the illustrated ones. Although the first front end cover 2 is illustrated in FIGS. 21A-21D, the second front end cover 2 may also be provided with a single lancing depth adjustment mark.

As shown in FIGS. 22A and 22B, the first front end cover 2 may be provided with a rib 29. The rib 29 serves to control the bulging amount of the skin to a certain level when the skin bulges due to negative pressure. Therefore, by the provision of the rib 29, the bulging degree of the skin during the suction can be stabilized, so that lancing can be performed reliably. Although the annular rib 29 is shown in FIGS. 22A and 22B, the rib may have any other configuration as long as it can control the bulging amount of the skin.

The present invention is not limited to a lancing apparatus including a lancet holder for holding the lancet, but is applicable to such a structure as shown in FIG. 23, in which a needle 40b' is integrally formed on a movable member 4' corresponding to the lancet holder.

Figure 24C:
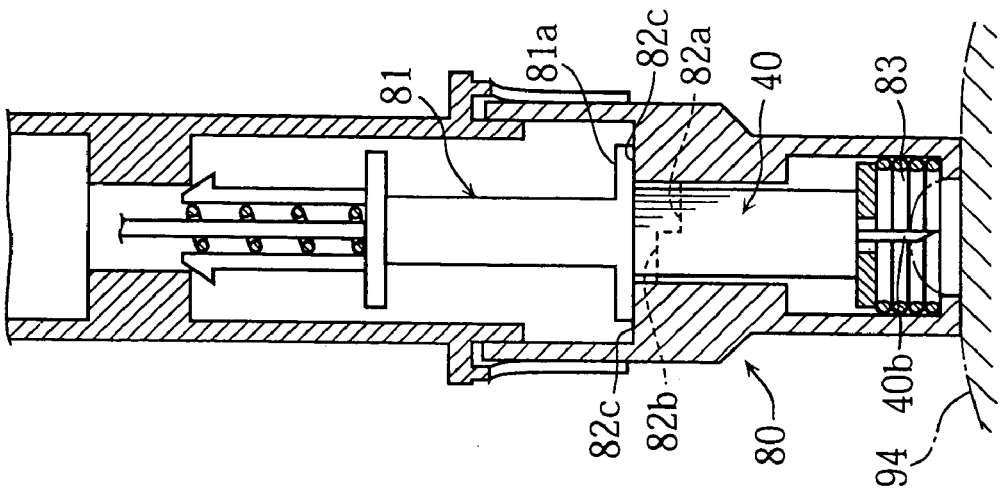
FIG. 24C is a longitudinal sectional view illustrating another example of lancing apparatus body in the state before lancing.
Figure 24B:
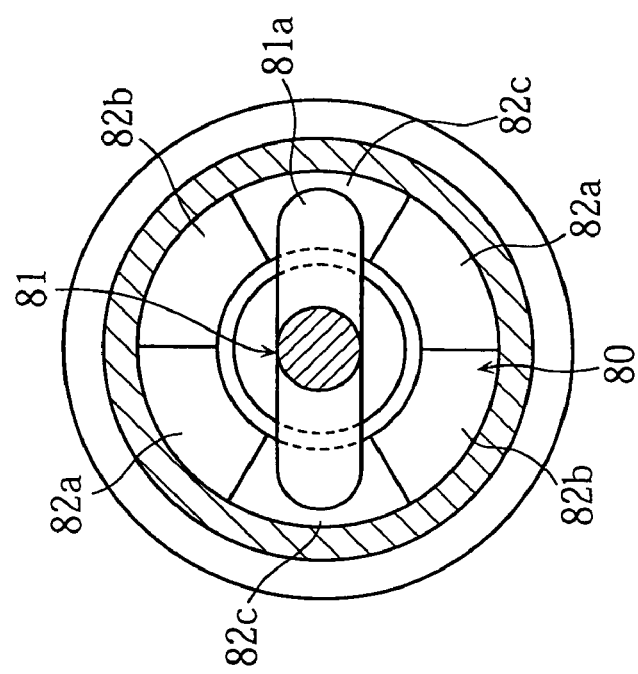
FIG. 24B is a sectional view taken along lines XXIVb-XXIVb in FIG. 24A.
Figure 24A:
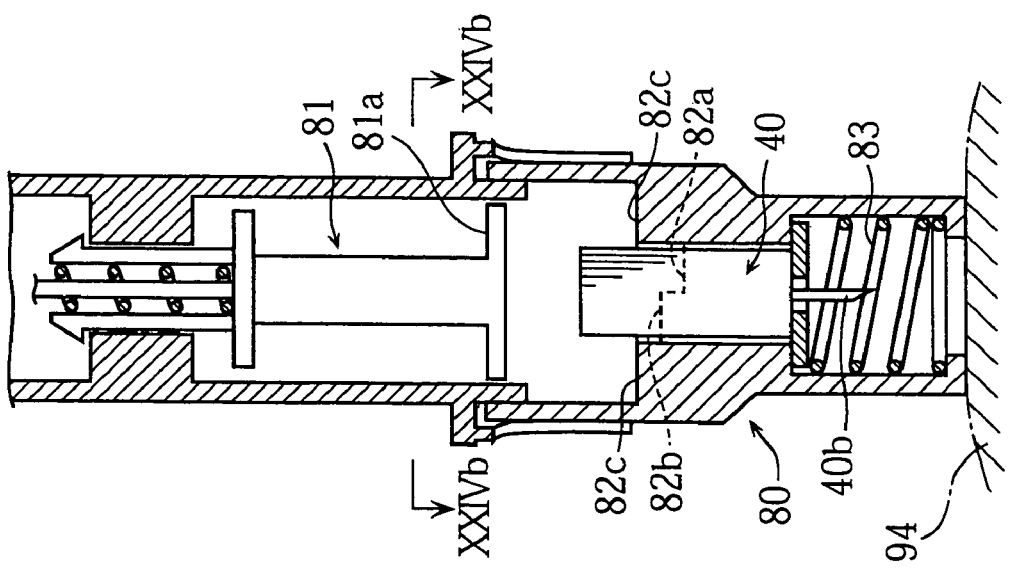
FIG. 24A is a longitudinal sectional view illustrating another example of lancing apparatus body in the state before lancing.

As shown in FIG. 24A, the present invention is also applicable to a structure in which the lancet 40 is held by a front end cover 80 for advance movement due to the pushing force of a hammer 81. As shown in FIGS. 24A and 24B, the front end cover 80 is provided with first through third contact surfaces 82a, 82b, 82c, which differ from each other in distance from the front end surface. The front end of the hammer 81 is formed with a plate-like contact portion 81a for contact with surfaces selected from the first through third contact surfaces 82a-82c. The front end of the front end cover 80 accommodates a coil spring 83, and the lancet 40 is held movably relative to the front end cover 80 while engaging the coil spring 83. The hammer 81 is moved by the latch mechanism described above. As shown in FIG. 24C, when the hammer 81 is released from the latched state, the hammer 81 moves toward the front-end side to come into contact with an end of the lancet 40, thereby pushing the lancet toward the front-end side. The movement of the hammer 81 is inhibited when the hammer comes into contact with selected ones of the first through the third contact surfaces 82a-82c. As a result, the movement of the lancet 40 toward the front end side is inhibited. Thus, the lancing depth in the skin 94 can be adjusted by selecting, from the first through the third contact surfaces 82a-82c, the surfaces to come into contact with the hammer 81. Thereafter, the lancet 40 moves in the reverse direction due to the resilient force of the coil spring 83, whereby the needle 40b is pulled out from the skin.

Figure 25:
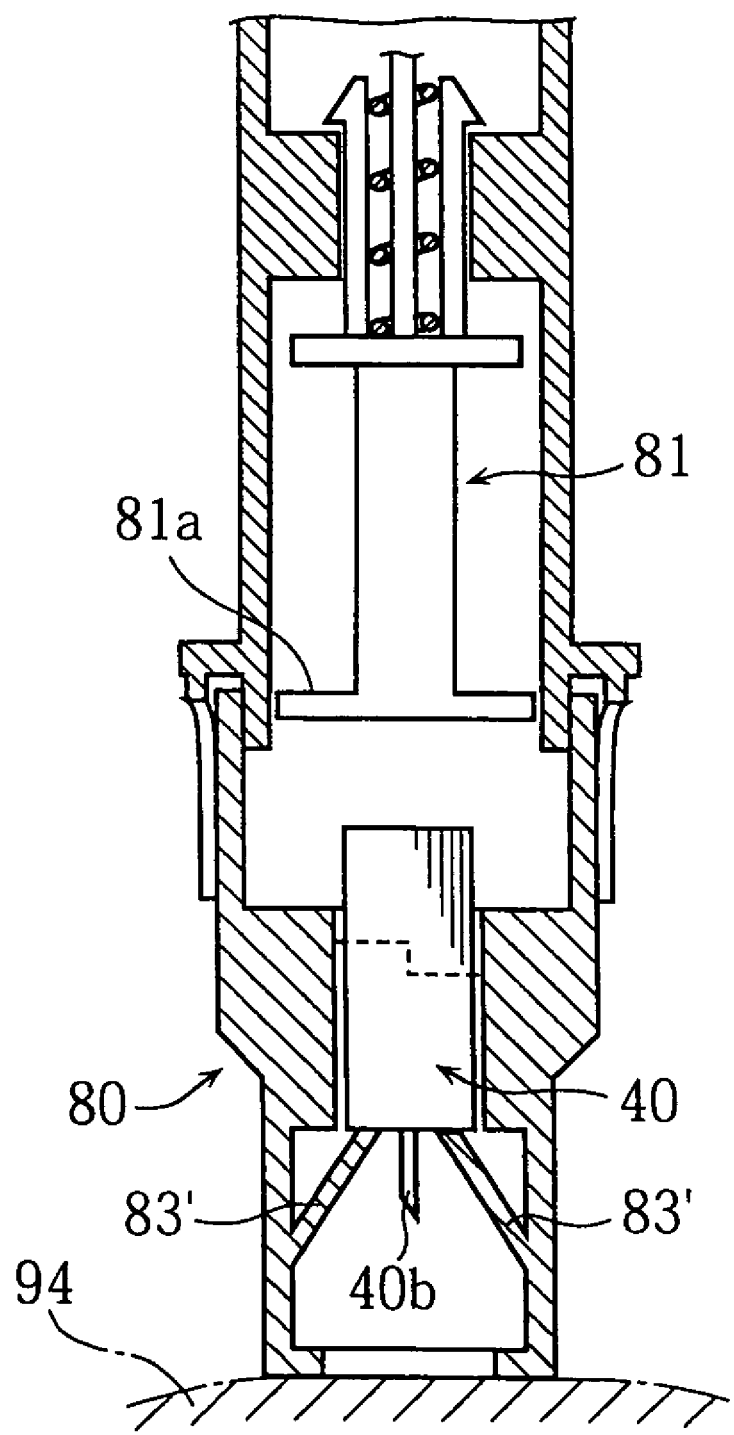
FIG. 25 is a longitudinal sectional view illustrating still another example of lancing apparatus body in the state before lancing.

As shown in FIG. 25, a leaf spring 83' may be employed instead of the coil spring so that the lancet 40 after the lancing is removed from the skin due to the resilient force of the leaf spring 83'. The leaf spring 83' may be formed integrally on the front end cover 80 as shown in the figure or may be formed separately from the front end cover 80 and attached to the front end cover 80.

In the foregoing embodiments, description is made of a structure in which the lancing depth is adjustable. However, in lancing, a first contact portion provided in a movable member such as a lancet holder may be brought into contact with a second contact portion provided in a front end cover, thereby keeping the lancing depth of the needle in the skin constant. This arrangement enables the lancing operation with stable lancing depth. In this case, when the front end cover is to be attached to the cover attach portion 51 shown in FIG. 9, the front end cover may be provided with one or a plurality of positioning marks (corresponding to the lancing depth adjustment marks 23a-23c, 33a-33c shown in FIG. 1). With this structure, the front end cover can be attached while properly positioning the projections (corresponding to the reference signs 22, 32 in FIG. 1) at the recess of the cover attach portion 51. The first and the second contact portions may have any configuration as long as they can engage with each other.

The invention claimed is:

1. A lancing apparatus comprising:
   an apparatus body including a housing and a movable member for advancing a needle, the movable member being arranged movably in the housing;
   a plurality of front end covers each for coming into contact with a portion to be lanced in lancing, the plurality of front end covers having different structures adapted for lancing different portions, the plurality of front end covers being removably attachable to a same portion of the apparatus body individually, one of the plurality of front end covers suitable for the portion to be lanced being selected in use for attachment to the apparatus body;
   a suction mechanism for generating negative pressure in said one of the plurality of front end covers attached to the apparatus body; and
   an operation member accommodating the housing,
   wherein the operation member is reciprocally movable axially of the housing relative to the housing, the suction mechanism being capable of adjusting the negative pressure for different values in accordance with number of times of the reciprocal movement of the operation member axially of the housing,
   wherein the movable member is provided with a first contact portion, whereas each of the plurality of front end covers is provided with a second contact portion for contacting the first contact portion for controlling movement of the movable member toward a front-end side,
   wherein lancing depth of the needle relative to the portion to be lanced is adjustable by selecting a contact position in the first contact portion or the second contact portion,
   wherein at least one of the first contact portion and the second contact portion includes a plurality of flat contact surfaces which differ from each other in distance from a front end surface of a selected front end cover when the front end cover is attached to the apparatus body.

2. The lancing apparatus according to claim 1, wherein the plurality of front end covers include one having a through-hole for passage of air.

3. The lancing apparatus according to claim 1, wherein the plurality of front end covers includes a first front end cover formed with a relatively large opening at an end for contacting a portion to be lanced, and a second front end cover formed with a relatively small opening at an end for contacting another portion to be lanced.

4. The lancing apparatus according to claim 3, wherein the second front end cover includes a through-hole for providing communication between an inside and an outside of the second front end cover.

5. The lancing apparatus according to claim 4, wherein the first front end cover includes a controlling portion for controlling a degree of bulging of the portion to be lanced when the portion to be lanced is bulged by generating negative pressure in the first front end cover by the suction mechanism.

6. The lancing apparatus according to claim 1, wherein the apparatus body is provided with a reference mark, whereas each of the plurality of front end covers is provided with one or a plurality of lancing depth adjustment marks; and wherein lancing depth of the needle relative to the portion to be lanced is adjustable by selecting an alignment state of the adjustment mark or the adjustment marks with the reference mark in attaching a selected one of the plurality of front end covers to the apparatus body.

7. The lancing apparatus according to claim 6, wherein each of the plurality of front end covers includes a plurality of projections; and wherein the housing includes a guide portion for engaging at least one of the projections to control movement of a selected one of the plurality of front end covers when the selected one of the plurality of front end covers is attached to the apparatus body, and an engagement portion for engaging at least one of the projections when the selected one of the plurality of front end covers is turned circumferentially relative to the housing.

8. The lancing apparatus according to claim 7, wherein at least one of the projections is positioned at the guide portion when the lancing depth adjustment mark or selected one of the lancing depth adjustment marks is aligned with the reference mark.

9. The lancing apparatus according to claim 1, wherein lancing depth of the needle in a portion to be lanced is kept constant by causing the first contact portion to contact the second contact portion when the movable member is advanced.

10. The lancing apparatus according to claim 1, wherein the needle is incorporated in the apparatus body as an integral part of a lancet; and wherein the lancet is mounted to the movable member in a state in which none of the plurality of front end covers is attached to the apparatus body.

11. A lancing apparatus with a lancing depth control function, which comprises:

an apparatus body including a housing and a movable member for advancing a needle, the movable member being arranged movably in the housing; and a front end cover attachable to the apparatus body for contacting a portion to be lanced in lancing;

wherein the movable member is provided with a first contact portion, whereas the front end cover is provided with a second contact portion for contacting the first contact portion for controlling movement of the movable member toward a front-end side, wherein a lancing depth of the needle relative to the portion to be lanced is adjustable by selecting a contact portion in the first contact portion or the second contact portion, wherein at least one of the first contact portion and the second contact portion includes a plurality of flat contact surfaces which differ from each other in distance from a front end surface of the front end cover when the front end cover is attached to the apparatus body, the plurality of flat contact surfaces being divided into groups each including cooperating ones of the plurality of flat contact surfaces, the cooperating ones of the plurality of flat contact surfaces being spaced from the front end surface of the front end cover by a same distance.

12. The lancing apparatus with a lancing depth control function according to claim 11, wherein the front end cover is removably attachable to the apparatus body;

wherein the apparatus body is provided with a reference mark, whereas the front end cover is provided with one or a plurality of lancing depth adjustment marks; and wherein lancing depth of the needle in the portion to be lanced is adjustable by selecting an alignment state of the adjustment mark or the adjustment marks with the reference mark in attaching the front end cover to the apparatus body.

13. The lancing apparatus with a lancing depth control function according to claim 12, wherein the front end cover includes a plurality of projections; and wherein the housing includes a guide portion for engaging at least one of the projections to control movement of the front end cover when the front end cover is attached to the apparatus body with the lancing depth adjustment mark or the lancing depth adjustment marks aligned with the reference mark, and an engagement portion for engaging at least one of the projections when the front end cover is turned circumferentially relative to the housing.

14. The lancing apparatus with a lancing depth control function according to claim 13, wherein at least one of the projections is positioned at the guide portion when the lancing depth adjustment mark or selected one of the lancing depth adjustment marks is aligned with the reference mark.

15. The lancing apparatus with a lancing depth control function according to claim 13, wherein the needle is incorporated in the apparatus body as an integral part of a lancet; and wherein the lancet is mounted to the movable member in a state in which the front end cover is not attached to the apparatus body.

16. The lancing apparatus with a lancing depth control function according to claim 11, wherein lancing depth of the needle in the portion to be lanced is kept constant by causing the first contact portion to contact the second contact portion when the movable member is advanced.

17. The lancing apparatus with a lancing depth control function according to claim 11, further comprising a suction mechanism for generating negative pressure in the front end cover attached to the apparatus body;

wherein the front end cover includes a controlling portion for controlling a degree of bulging of the portion to be lanced when the portion to be lanced is bulged by generating negative pressure in the front end cover by the suction mechanism.

18. A lancing apparatus comprising:

an apparatus body including a housing and a movable member for advancing a needle, the movable member being arranged in the housing; and a plurality of front end covers each for coming into contact with a portion to be lanced in lancing, the plurality of front end covers having different structures adapted for lancing different portions, the plurality of front end covers being removably attached to a same portion of the apparatus body individually;

wherein one of the front end covers suitable for the portion to be lanced is selected in use for attachment to the apparatus body, wherein at least one of the front end covers is formed with a pressure adjuster for preventing application of negative pressure to the portion to be lanced, the pressure adjuster providing communication between an inside of said one of the front end covers and an outside of the lancing apparatus when said one of the front end covers is attached to the apparatus body.

19. The lancing apparatus according to claim 18, wherein the pressure adjuster is a through-hole.

20. A lancing apparatus with a lancing depth control function, which comprises:

an apparatus body including a housing and a movable member for advancing a needle, the movable member being arranged movably in the housing; and a front end cover rotatably attached to the apparatus body for contacting a portion to be lanced in lancing;

wherein the movable member is provided with a first contact portion, whereas the front end cover is provided with a second contact portion for contacting the first contact portion for controlling movement of the movable member toward a front-end side, wherein a lancing depth of the needle relative to the portion to be lanced is adjustable by selecting a contact portion in the first contact portion or the second contact portion, wherein at least one of the first contact portion and the second contact portion includes a plurality of flat contact surfaces which differ from each other in distance from a front end surface of the front end cover when the front end cover is attached to the apparatus body, wherein the selection of the contact portion in the first contact portion or the second contact portion is performed by rotating the front end cover relative to the apparatus body.

* * * * *